(12) United States Patent
Wittek et al.

(10) Patent No.: US 7,651,742 B2
(45) Date of Patent: Jan. 26, 2010

(54) LIQUID-CRYSTALLINE MEDIUM AND LIQUID-CRYSTAL DISPLAY COMPRISING 1,2-DIFLUOROETHENE COMPOUNDS

(75) Inventors: Michael Wittek, Darmstadt (DE); Markus Czanta, Darmstadt (DE); Harald Hirschmann, Darmstadt (DE); Volker Reiffenrath, Roβdorf (DE)

(73) Assignee: Merck Patent GmbH, Darmstadt (DE)

( * ) Notice: Subject to any disclaimer, the term of this patent is extended or adjusted under 35 U.S.C. 154(b) by 32 days.

(21) Appl. No.: 11/917,284

(22) PCT Filed: May 18, 2006

(86) PCT No.: PCT/EP2006/004708

§ 371 (c)(1),
(2), (4) Date: Dec. 12, 2007

(87) PCT Pub. No.: WO2006/133783

PCT Pub. Date: Dec. 21, 2006

(65) Prior Publication Data

US 2008/0260971 A1    Oct. 23, 2008

(30) Foreign Application Priority Data

Jun. 13, 2005  (DE)  ........................ 10 2005 027 171

(51) Int. Cl.
| | |
|---|---|
| C09K 19/34 | (2006.01) |
| C09K 19/30 | (2006.01) |
| C09K 19/12 | (2006.01) |
| C09K 19/20 | (2006.01) |
| C07D 309/00 | (2006.01) |

(52) U.S. Cl. .............. 428/1.1; 252/299.61; 252/299.63; 252/299.66; 252/299.67; 549/426; 549/427; 549/428

(58) Field of Classification Search .................. 428/1.1; 252/299.61, 299.63, 299.66, 299.67; 549/426, 549/427, 428
See application file for complete search history.

(56) References Cited

U.S. PATENT DOCUMENTS

| | | | |
|---|---|---|---|
| 4,601,547 A * | 7/1986 | Shingu ........................ 349/165 |
| 5,380,461 A | 1/1995 | Sato et al. |
| 5,914,071 A | 6/1999 | Shinya et al. |
| 6,207,076 B1 * | 3/2001 | Koga et al. ............. 252/299.63 |
| 6,565,932 B2 * | 5/2003 | Iwamatsu et al. ............ 428/1.1 |
| 7,105,210 B2 * | 9/2006 | Heckmeier et al. ........... 428/1.1 |
| 7,361,388 B2 * | 4/2008 | Kirsch et al. ................. 428/1.1 |
| 2001/0004108 A1 | 6/2001 | Iwamatsu et al. |
| 2002/0028306 A1 | 3/2002 | Kirsch et al. |
| 2004/0173776 A1 | 9/2004 | Heckmeier et al. |
| 2006/0289829 A1 | 12/2006 | Kirsch et al. |

FOREIGN PATENT DOCUMENTS

| | | |
|---|---|---|
| DE | 101 24 480 A1 | 1/2002 |
| DE | 101 51 491 A1 | 5/2002 |
| DE | 101 55 073 A1 | 8/2002 |
| DE | 102004 008638 A1 | 9/2004 |
| EP | 0 560 382 A | 9/1993 |
| EP | 1 215 270 A | 6/2002 |
| EP | 1 416 030 A | 5/2004 |
| JP | 03 041037 A | 2/1991 |
| JP | 03 294386 A | 12/1991 |
| JP | 06 329566 A | 11/1994 |
| JP | 9-208958 | 8/1997 |
| JP | 11-302651 | 11/1999 |
| JP | 2002180048 A2 | 6/2002 |
| JP | 2005-206617 A | 8/2005 |
| WO | WO 2004 106460 A | 12/2004 |

OTHER PUBLICATIONS

English translation by computer for JP 06-329566 (1994), http://www4.ipdl.inpit.go.jp/Tokujitu/PAJdetail.ipdl?N0000=60&N0120=01&N2001=2&N3001=H06-329566.*
English translation by computer for JP 09-208958(1997), http://www4.ipdl.inpit.go.jp/Tokujitu/PAJdetail.ipdl?N0000=60&N0120=01&N2001=2&N3001=H09-208958.*
English translation by computer for JP 11-302651(1999), http://www4.ipdl.inpit.go.jp/Tokujitu/PAJdetail.ipdl?N0000=60&N0120=01&N2001=2&N3001=H11-302651.*
English translation by computer for JP 2005-206617(2005), http://www4.ipdl.inpit.go.jp/Tokujitu/PAJdetail.ipdl?N0000=60&N0120=01&N2001=2&N3001=2005-206617.*
English translation by computer for JP 2002-218048(2002), http://www4.ipdl.inpit.go.jp/Tokujitu/PAJdetail.ipdl?N0000=60&N0120=01&N2001=2&N3001=2002-180048.*
DE file history P4006921.4-43, compound data submitted to the DPMA (faxed Sep. 28, 2005).

* cited by examiner

*Primary Examiner*—Shean C Wu
(74) *Attorney, Agent, or Firm*—Millen, White, Zelano, Branigan, P.C.

(57) ABSTRACT

The present invention relates to a liquid-crystalline medium comprising 1,2-difluoroethene compounds of the general formula I, in which $R^1$, ring A, $Z^1$, $Z^2$, m, X and $L^{1-6}$ are as defined in claim 1. The invention also relates to the use of the medium for electro-optical purposes and to displays containing this medium. Novel 1,2-difluoroethene compounds having 3 or more rings are disclosed.

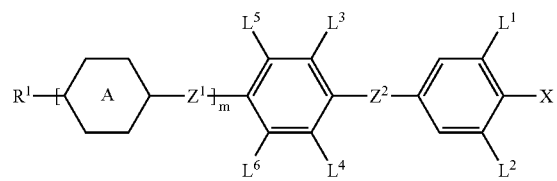

28 Claims, No Drawings

LIQUID-CRYSTALLINE MEDIUM AND LIQUID-CRYSTAL DISPLAY COMPRISING 1,2-DIFLUOROETHENE COMPOUNDS

The present invention relates to a liquid-crystalline medium comprising 1,2-difluoroethene compounds, and to the use thereof for electro-optical purposes, and to displays containing this medium. Novel 1,2-difluoroethene compounds according to the invention are disclosed.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure. In addition, there are also cells which operate with an electric field parallel to the substrate and liquid-crystal plane, such as the IPS (in-plane switching) cells. The TN, STN and IPS cells, in particular, are currently commercially interesting areas of application for the media according to the invention.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and relatively low vapour pressure are desired.

Matrix liquid-crystal displays of this type are known. Examples of non-linear elements which can be used to individually switch the individual pixels are active elements (i.e. transistors). The term "active matrix" is then used, where a distinction can be made between two types:

1. MOS (metal oxide semiconductor) or other diodes on silicon wafers as substrate
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are backlit.

The term MLC displays here encompasses any matrix display with integrated non-linear elements, i.e., besides the active matrix, also displays with passive elements, such as varistors or diodes (MIM=metal-insulator-metal).

MLC displays of this type are particularly suitable for TV applications (for example pocket television sets) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not satisfy today's requirements. In addition to liquid-crystal displays which use backlighting, i.e. are operated transmissively and if desired transflectively, reflective liquid-crystal displays are also particularly interesting. These reflective liquid-crystal displays use the ambient light for information display. They thus consume significantly less energy than backlit liquid-crystal displays having a corresponding size and resolution. Since the TN effect is characterised by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence ($\Delta n$) is necessary in order to achieve low optical retardation (d·$\Delta n$). This low optical retardation results in usually acceptable low viewing-angle dependence of the contrast (cf. DE 30 22 818).

In reflective displays, the use of liquid crystals of low birefringence is even more important than in transmissive displays since the effective layer thickness through which the light passes is approximately twice as large in reflective displays as in transmissive displays having the same layer thickness.

Thus there continues to be a great demand for MLC displays having very high specific resistance at the same time as a large working-temperature range, short response times, even at low temperatures, and a low threshold voltage which do not exhibit these disadvantages or only do so to a lesser extent.

In the case of TN (Schadt-Helfrich) cells, media are desired which facilitate the following advantages in the cells:
- extended nematic phase range (in particular down to low temperatures)
- storage-stable, even at extremely low temperatures
- the ability to switch at extremely low temperatures (outdoor use, automobile, avionics)
- increased resistance to UV radiation (longer life)

The media available from the prior art do not enable these advantages to be achieved while simultaneously retaining the other parameters.

In the case of supertwisted (STN) cells, media are desired which facilitate greater multiplexability and/or a lower threshold voltage and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention is based on the object of providing media, in particular for MLC, TN or STN displays of this type, which do not have the above-mentioned disadvantages or only do so to a lesser extent, and preferably at the same time have very high specific resistance values and low threshold voltages.

It has now been found that this object can be achieved if media according to the invention are used in displays. The media according to the invention are distinguished by very low rotational viscosities $\gamma_1$ in combination with a high clearing point ($T_{clp.}$) and good low-temperature properties.

JP 06329566 A and U.S. Pat. No. 5,380,461 A describe fluorinated stilbenes which are in some cases related to the components of the mixtures of the present invention. Synthetic methods for this class of compound are disclosed therein.

The invention relates to a liquid-crystalline medium of positive dielectric anisotropy based on a mixture of compounds, characterised in that it comprises one or more compounds of the formula I

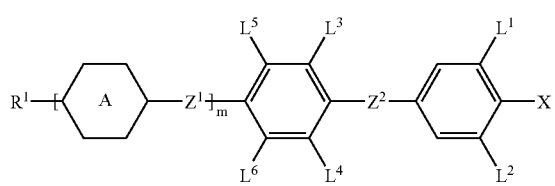

I in which
R$^1$ denotes a halogenated or unsubstituted alkyl or alkoxy radical having 1 to 15 C atoms, where, in addition, one or more CH$_2$ groups in these radicals may each, independently of one another, be replaced by —C≡C—, —CH=CH—, —O—, —CO—O— or —O—CO— in such a way that O atoms are not linked directly to one another, ring A denotes a ring system of the formulae

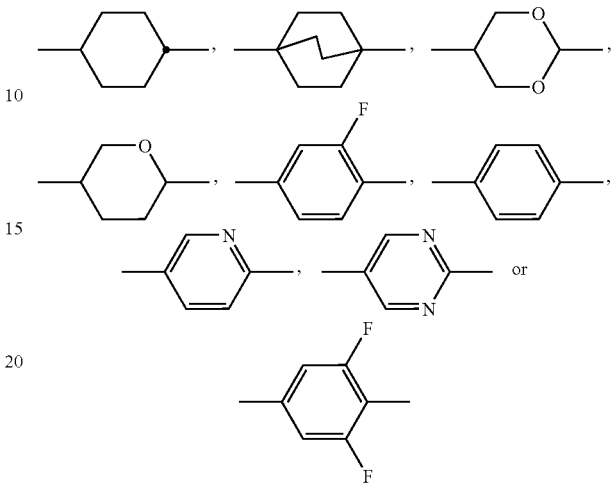

pointing to the left or right,

Z$^1$, Z$^2$ denote a single bond, —C≡C—, —CF=CF—, —CH=CH—, —CF$_2$O— or —CH$_2$CH$_2$—, where at least one group from Z$^1$ and Z$^2$ denotes the group —CF=CF—, X denotes F, Cl, CN, SF$_5$ or a halogenated or unsubstituted alkyl or alkoxy radical having 1 to 15 C atoms, where, in addition, one or more CH$_2$ groups in these radicals may each, independently of one another, be replaced by —C≡C—, —CH=CH—, —O—, —CO—O— or —O—CO— in such a way that O atoms are not linked directly to one another, L$^1$, L$^2$, L$^3$, L$^4$, L$^5$ and L$^6$ each, independently of one another, denote H or F, and m denotes 0, 1 or 2.

Preferably, 2, 3 or 4 of the substituents L$^1$, L$^2$, L$^3$ and L$^4$ in the formula I denote hydrogen and the others denote F. Particular preference is given to media comprising compounds of the formula I in which L$^5$ and L$^6$=H. In the case where m=0, L$^1$ or L$^2$ is particularly preferably F. In the case where m=1 or 2, L$^1$ and L$^2$ are particularly preferably H. X preferably denotes F, Cl, OCF$_3$, CF$_3$, SF$_5$, OCHF$_2$, OC$_2$F$_5$, OC$_3$F$_7$, OCHFCF$_3$, OCF$_2$CHFCF$_3$ or an alkyl radical having 1 to 8 C atoms. Very particular preference is given to compounds in which X denotes a substituent F, Cl, OCF$_3$ or a straight-chain alkyl radical having 1 to 6 C atoms. R$^1$ preferably stands for an unsubstituted, straight-chain 1-6 C alkyl or alkoxy radical or a corresponding 2-6 C alkenyl radical, very particularly for a 1-6 C n-alkyl radical.

In order to achieve mixtures having particularly high dielectric anisotropy, the substituent X preferably denotes F, Cl, OCF$_3$, CF$_3$, SF$_5$, OCHF$_2$, OC$_2$F$_5$, OC$_3$F$_7$, OCHFCF$_3$ or OCF$_2$CHFCF$_3$, particularly preferably F, CF$_3$ or OCF$_3$, and very particularly preferably F or OCF$_3$.

The linking unit Z$^1$ preferably denotes a single bond or —CF=CF—. The linking unit Z$^2$ preferably denotes —CF=CF— or —CF$_2$O—. m is preferably 0 or 1.

The invention furthermore relates to compounds of the formula I in which m denotes 1 or 2, and Z$^2$ denotes a —CF=CF— bridge (compounds Ia). In the compounds of the formula I according to the invention, the other structural moieties $R^1$, ring A, $Z^1$, X and $L^{1-6}$ have the meanings indicated above and the preferred meanings indicated above.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimise its threshold voltage and/or its viscosity.

In the pure state, the compounds of the formula I are colourless and form liquid-crystalline mesophases in a temperature range which is favourably located for electro-optical use. They are stable chemically and thermally.

Alone and in mixtures, the compounds according to the invention have a particularly low rotational viscosity compared with other compounds having comparable physical-chemical properties. In addition, they exhibit very good overall properties, in particular with respect to the ratio of the rotational viscosity to the clearing point ($\gamma_1$/clp.).

In the case where m=1 or 2 and $Z^1$ denotes a —CF=CF— group, the ring A is preferably a ring system selected from the formulae

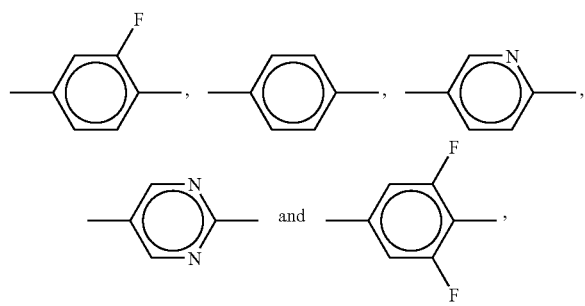

where the rings may point to both sides.

In the case where m=1 or 2 and $Z^2$ denotes a —CF=CF— group, the ring A is preferably a ring system selected from the formulae

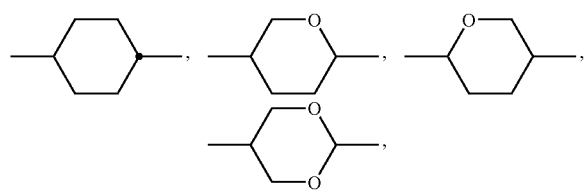

and

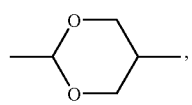

in particular from the formulae

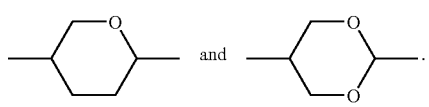

Preferred compounds in accordance with the invention are characterised in that, independently of one another, m denotes 1,
$Z^2$ denotes —CF=CF— and $Z^1$ denotes a single bond,
X denotes F, —OCF$_3$, —CF$_3$, CN, 1-6 C n-alkyl or 1-6 C n-alkoxy, in particular F or —OCF$_3$,
$L^5$ $L^6$ denote H, or
$R^1$ denotes 1-7 C alkyl or 2-7 C alkylene.

In the case where $Z^2$ denotes a —CF=CF— group, $L^3$ and $L^4$ are preferably H.

Particularly preferred compounds according to the invention are characterised in that precisely one group from $Z^1$ and $Z^2$ represents a —CF=CF— group. Consequently, particularly preferred compounds according to the invention are those of the general formula Ib:

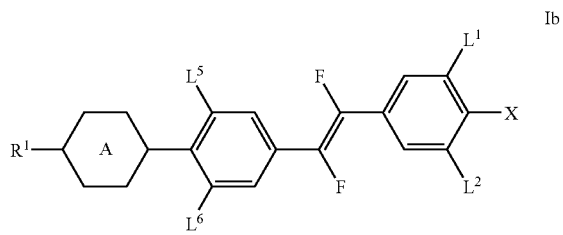

Ib in which $R^1$, ring A, X, $L^1$, $L^2$, $L^5$ and $L^6$ are as defined above.

Particularly preferred compounds of formula I, wherein ring A is a tetrahydropyran ring, are compounds of formula Ic:

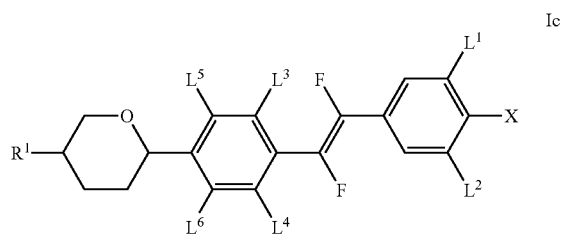

Ic

If $R^1$ in formula I denotes an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl preferably denotes straight-chain 2-oxapropyl (=methoxymethyl), 2-(=ethoxymethyl) or 3-oxabutyl(=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ denotes an alkyl radical in which one CH$_2$ group has been replaced by —CH=CH—, this may be straight-chain or branched. It is preferably straight-chain and has 2 to 10 C atoms. Accordingly, it denotes in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ denotes an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. Accordingly, they denote in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonyl methyl, butoxycarbonyl methyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ denotes an alkyl radical in which one $CH_2$ group has been replaced by unsubstituted or substituted —CH=CH— and an adjacent $CH_2$ group has been replaced by CO or CO—O or O—CO, this may be straight-chain or branched. It is preferably straight-chain and has 4 to 12 C atoms. Accordingly, it denotes in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, or 9-methacryloyloxynonyl.

If $R^1$ denotes an alkyl or alkenyl radical which is monosubstituted by CN or $CF_3$, this radical is preferably straight-chain. The substitution by CN or $CF_3$ is in any desired position.

If $R^1$ denotes an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds containing branched wing groups $R^1$ may occasionally be of importance owing to better solubility in the conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ are isopropyl, 2-butyl(=1-methylpropyl), isobutyl(=2-methylpropyl), 2-methylbutyl, isopentyl(=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy, 1-methylheptyloxy.

If $R^1$ represents an alkyl radical in which two or more $CH_2$ groups have been replaced by —O— and/or —CO—O—, this may be straight-chain or branched. It is preferably branched and has 3 to 12 C atoms. Accordingly, it denotes in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl, 5,5-bis(ethoxycarbonyl)hexyl.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

Suitable processes for the preparation are outlined in Scheme 1 and Scheme 2.

Scheme 1. Preparation of the 1,2-difluoroethene compounds. $Ar^1$ and $Ar^2$ stand, for example, for substituted benzene rings.

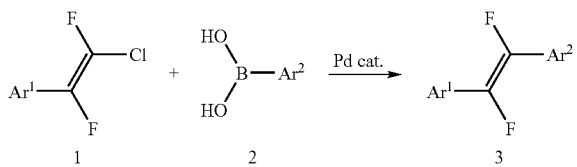

Scheme 2. Preparation of the chlorodifluoroethene compounds 1.

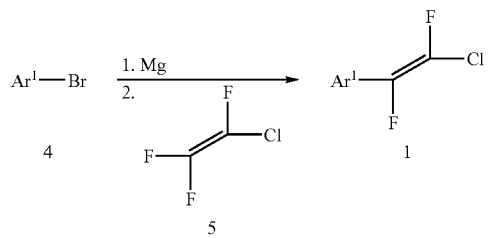

Scheme 1 shows how the difluoroethene compounds 3 according to the invention can be prepared by palladium-catalysed linking of a chloro-difluoroethene compound of the formula 1 to a boronic acid compound of the formula 2. The formula 3 is analogous to formula I. The radicals $Ar^1$ and $Ar^2$ correspondingly represent substituted, aromatic ring systems.

The starting compounds of the formula 1 can be prepared from an aryl halide 4 by halogen-metal exchange and reaction with chlorotrifluoroethylene. In the synthesis strategy shown, the desired E isomer of the formula 3 is formed in an excess to the Z isomer. The desired isomer can easily be isolated by chromatography and by crystallisation.

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high specific resistance located in the cell) which contain media of this type, and to the use of these media for electro-optical purposes.

The liquid-crystal mixtures according to the invention enable a significant broadening of the available parameter latitude. The achievable combinations of clearing point, viscosity at low temperature, thermal stability and dielectric anisotropy are far superior to previous materials from the prior art.

The compounds of the formula I are, in accordance with the invention, combined with further highly polar components where $\Delta\epsilon>8$ and with one or more neutral components ($-1.5<\Delta\epsilon<3$), at least some of which simultaneously have low optical anisotropy ($\Delta n<0.08$), in order to obtain the liquid-crystalline media.

The liquid-crystal mixtures according to the invention, while retaining the nematic phase down to $-20°$ C. and preferably down to $-30°$ C., particularly preferably down to $-40°$ C., enable a clearing point above $60°$ C., preferably above $65°$ C., particularly preferably above $70°$ C., simultaneously dielectric anisotropy values $\Delta\epsilon$ of $\geq 3$, preferably $\geq 5$, in particular also $\geq 7$, and a high value for the specific resistance to be achieved, enabling excellent STN and MLC displays to be obtained. In particular, the mixtures are characterised by very low rotational viscosities. The rotational viscosities $\gamma_1$ are below 90 mPa·s, preferably below 80 mPa·s, particularly preferably below 70 mPa·s. At the same time, the operating voltages, depending on the selected dielectric anisotropy of the medium, have low values.

It goes without saying that, through a suitable choice of the components of the mixtures according to the invention, it is also possible for higher clearing points (for example above $90°$ C.) to be achieved at higher threshold voltages or lower clearing points to be achieved at lower threshold voltages with retention of the other advantageous properties. At viscosities correspondingly increased only slightly, it is likewise possible to obtain mixtures having higher $\Delta\epsilon$ and thus low thresholds or mixtures having higher clearing points. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (DE 3022818 A1), a lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $v_{20}$ at $20°$ C. is preferably $<60$ mm$^2$·s$^{-1}$, particularly preferably $<50$ mm$^2$·s$^{-1}$. The rotational viscosity $\gamma_1$ of the mixtures according to the invention at $20°$ C. is preferably $<80$ mPa·s, particularly preferably $<70$ mPa·s. The nematic phase range preferably has a width of at least $90°$ C., in particular at least $100°$ C. This range preferably extends at least from $-20°$ to $+70°$ C.

A short response time is desired in liquid-crystal displays. This applies in particular to displays for video reproduction. For displays of this type, response times (total: $t_{on}+t_{off}$) of at most 16 ms are required. The upper limit for the response time is determined by the image refresh frequency. Besides the rotational viscosity $\gamma_1$, the tilt angle also influences the response time.

Measurements of the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than analogous mixtures comprising cyanophenylcyclohexanes of the formula

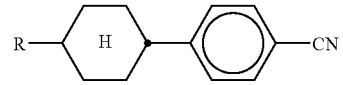

or esters of the formula

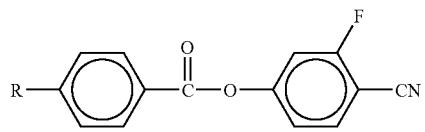

instead of the compounds of the formula I.

Particularly preferred liquid-crystalline media comprise one or more compounds from the formulae I-1 to I-30:

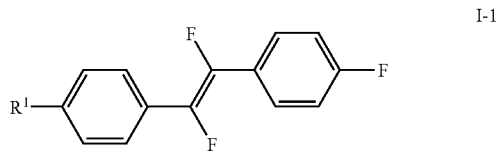

I-1

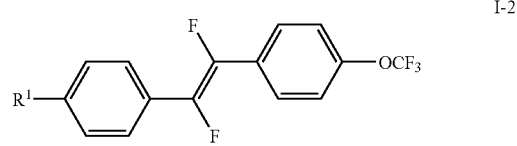

I-2

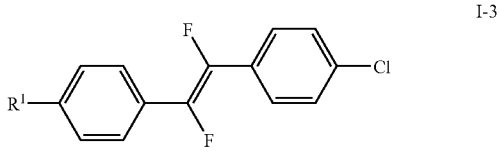

I-3

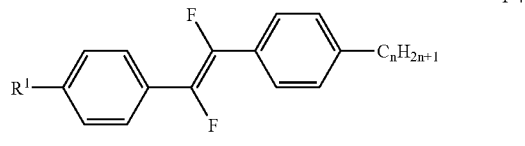

I-4

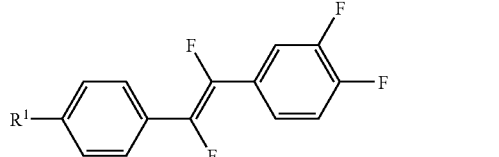

I-5

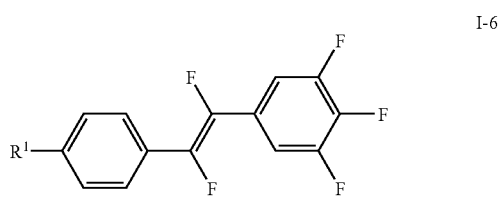

I-6

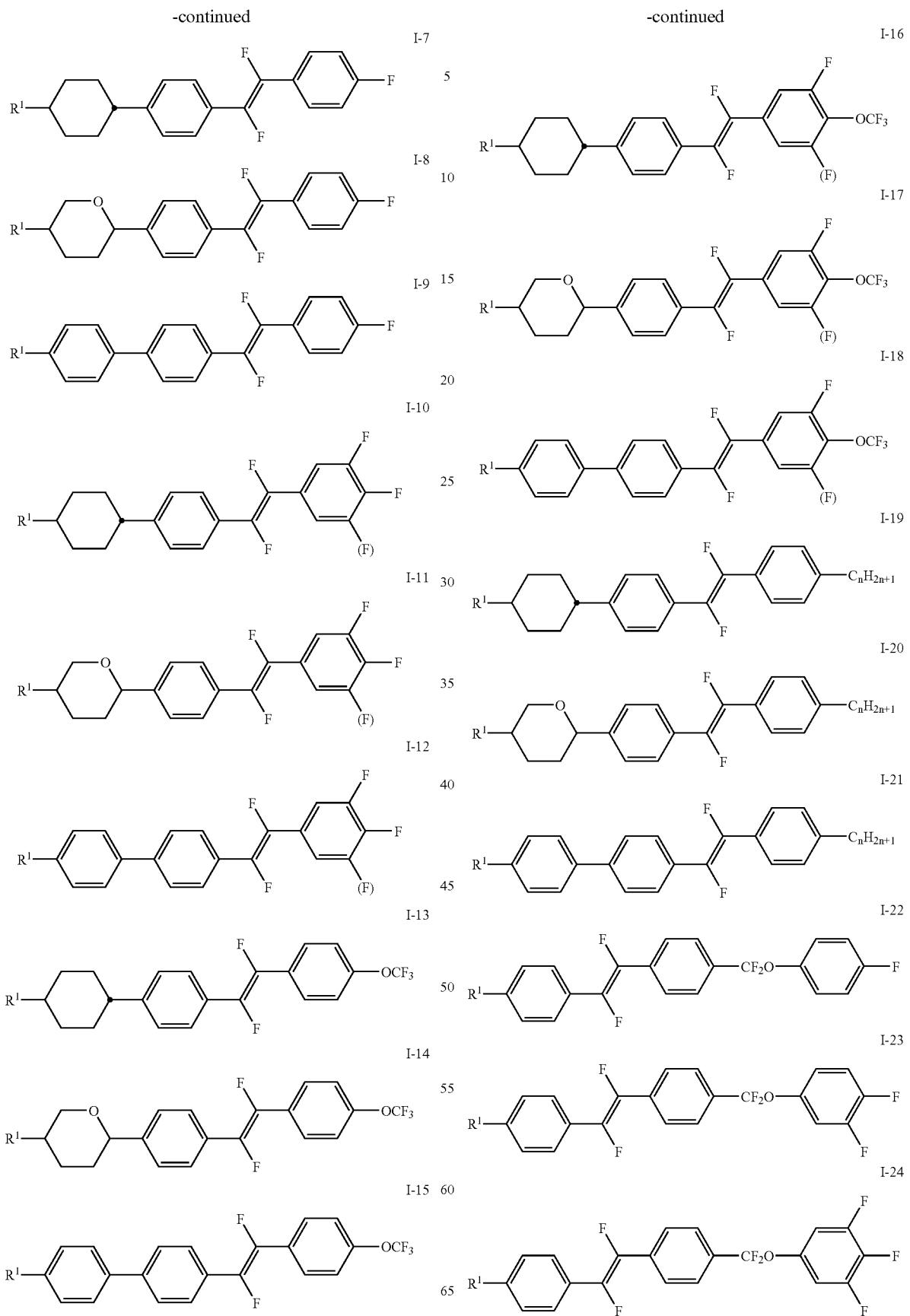

-continued

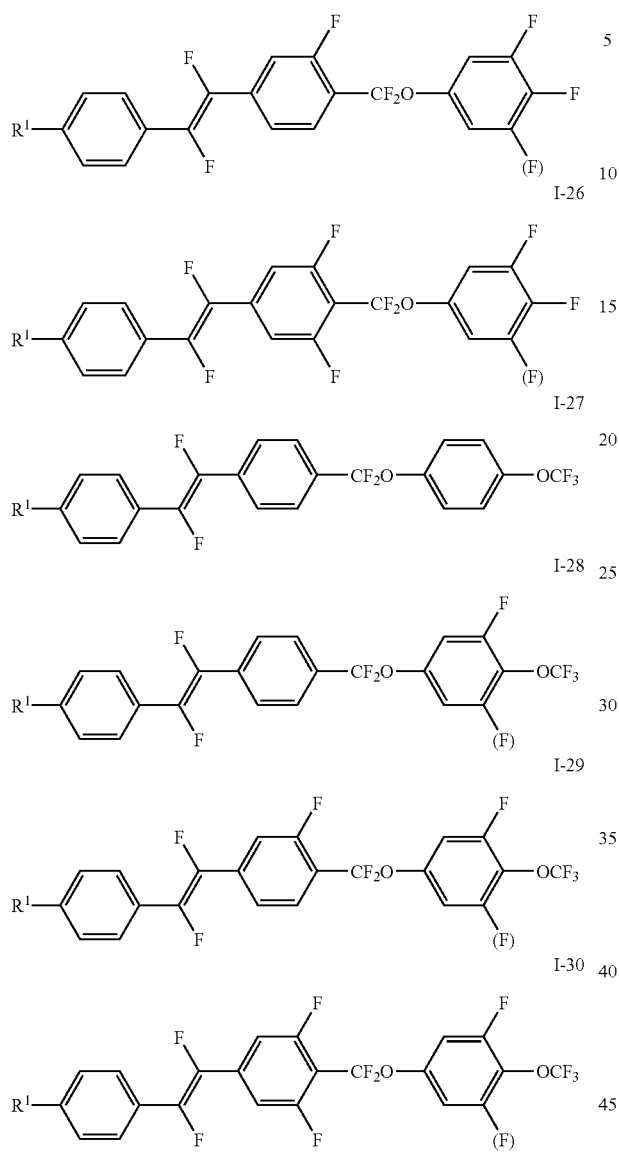

in which R¹ has the meaning indicated in formula I.

Of these preferred compounds, particularly preferred bicyclic compounds (m=0) are those of the formulae I-1, I-2, I-3, I-4 and I-5, very particularly those of the formulae I-1, I-2 and I-4. Of the tricyclic compounds, particular preference is given to those of the formulae I-7, I-8, I-10, I-13, I-14, I-16, I-19, I-22, I-23, I-24, I-27 and I-28, very particularly those of the formulae I-8 and I-14.

Preferred embodiments of the liquid-crystalline media according to the invention are indicated below:

The liquid-crystalline medium is characterised in that the proportion of compounds of the formula I in the mixture as a whole is from 0.5 to 40% by weight, preferably from 4 to 20% by weight.

The medium comprises one, two or more compounds of the formulae I-1 to I-30;

The medium additionally comprises one or more compounds selected from the group consisting of the general formulae II to VI:

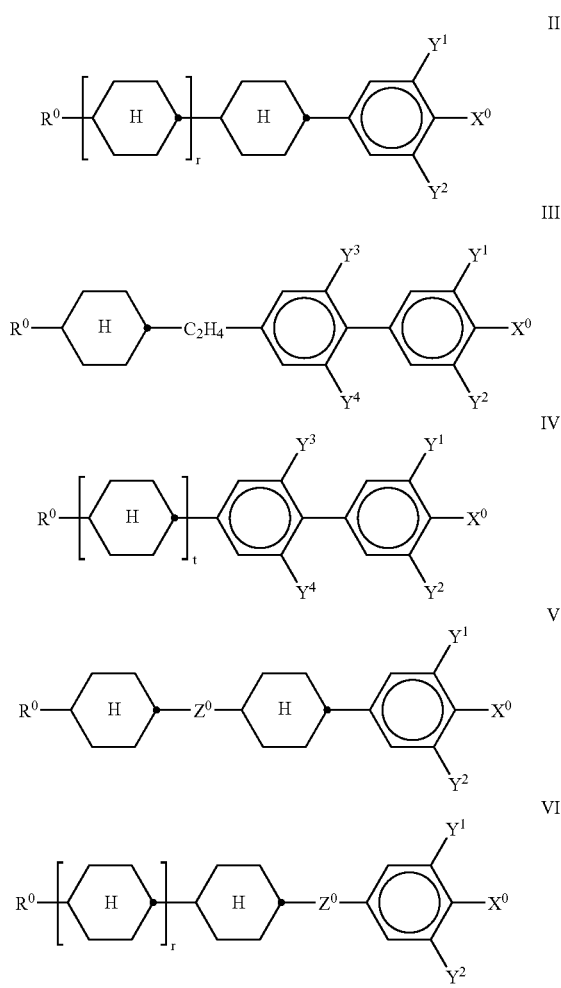

in which the individual radicals have the following meanings:

$R^0$ n-alkyl, alkoxy, oxaalkyl, fluoroalkyl or alkenyl, each having up to 9 C atoms, $X^0$ F, Cl, halogenated alkyl, halogenated alkenyl, halogenated oxaalkyl, halogenated alkenyloxy or halogenated alkoxy having up to 6 C atoms, $Z^0$ —$C_2F_4$—, —CF=CF—, —$C_2H_4$—, —$(CH_2)_4$—, —$OCH_2$—, —$CH_2O$—, —$CF_2O$— or —$OCF_2$—, $Y^1$ to $Y^4$ each, independently of one another, H or F, r 0 or 1, and t 0, 1 or 2.

The compound of the formula IV is preferably

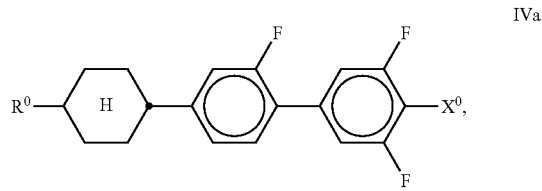

-continued

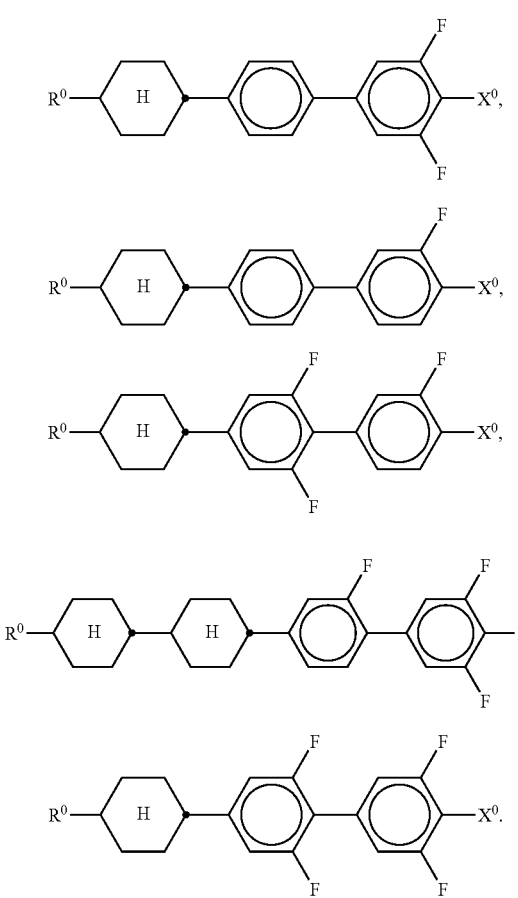

The medium additionally comprises one or more compounds selected from the group consisting of the general formulae VII to XIII:

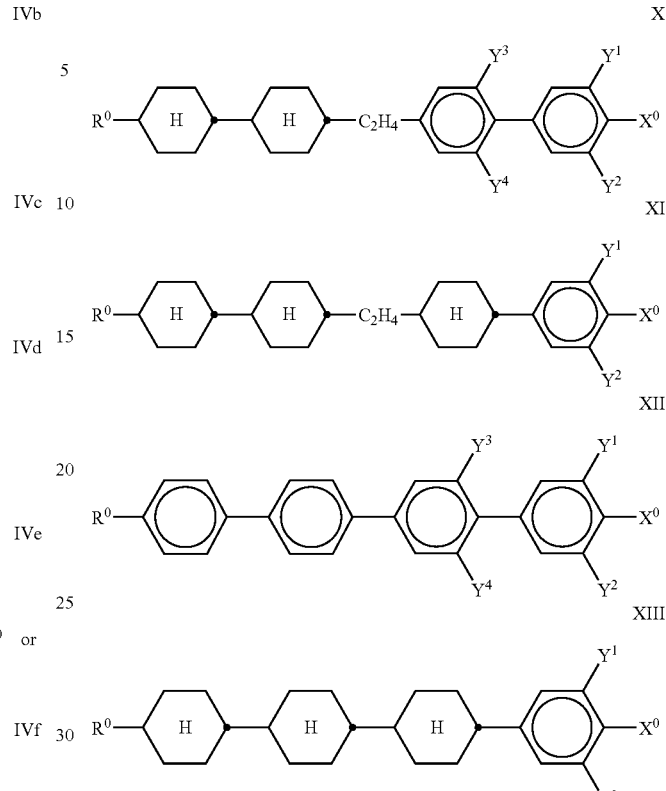

in which
R⁰ denotes n-alkyl, oxaalkyl, fluoroalkyl or alkenyl, each having up to 9 C atoms,
X⁰ denotes F, Cl, halogenated alkyl, halogenated alkenyl, halogenated alkenyloxy or halogenated alkoxy having up to 6 C atoms, and
$Y^1$ to $Y^4$ each, independently of one another, denote H or F.

X⁰ here is preferably F, Cl, $CF_3$, $OCF_3$ or $OCHF_2$. R⁰ here preferably denotes alkyl, alkoxy, oxaalkyl, fluoroalkyl or alkenyl, each having up to 6 C atoms.

The medium additionally comprises one or more compounds of the formulae E-a to E-d

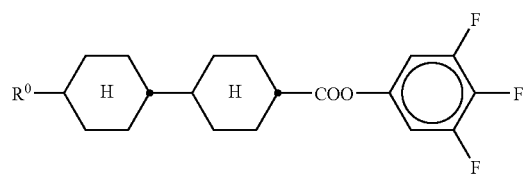

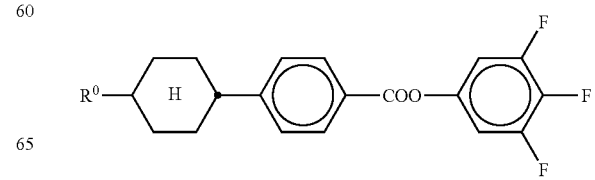

-continued

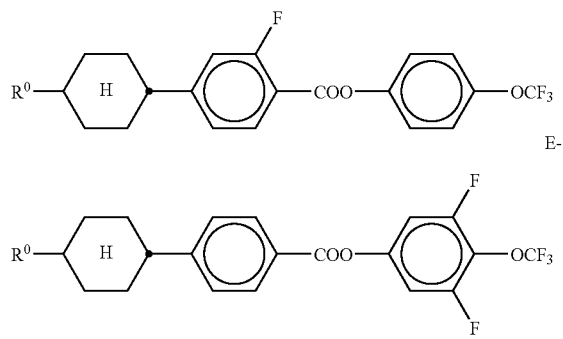

in which

R⁰ denotes n-alkyl, oxaalkyl, fluoroalkyl or alkenyl, each having up to 9 C atoms.

The proportion of compounds of the formula I in the mixture as a whole is from 0.5 to 40% by weight, particularly preferably from 1 to 30% by weight;

The proportion of the compounds of the formulae E-a to E-d is preferably 5-30% by weight, in particular 5-25% by weight;

The proportion of compounds of the formulae I to VI together in the mixture as a whole is at least 30% by weight;

The proportion of compounds of the formulae II to VI in the mixture as a whole is from 30 to 80% by weight;

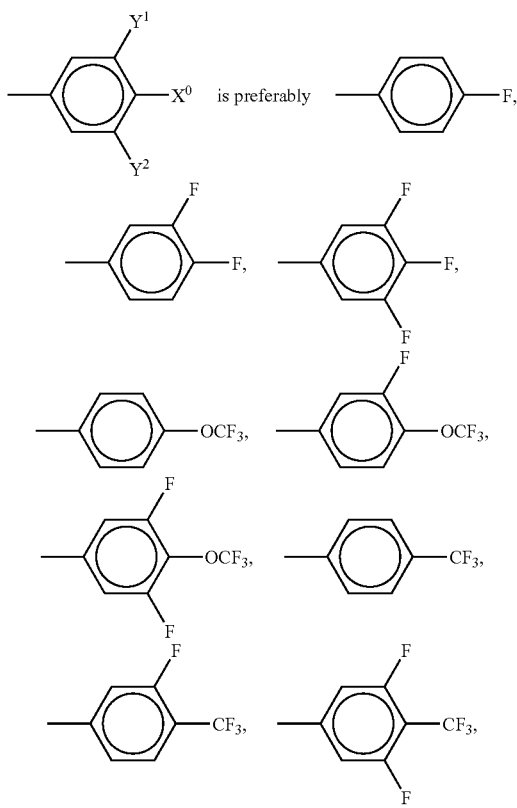

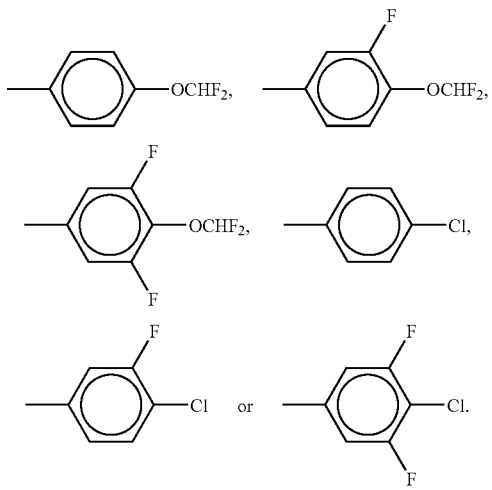

The medium comprises compounds of the formulae II, III, IV, V and/or VI;

R⁰ in all compounds is preferably straight-chain alkyl or alkenyl having 2 to 7 C atoms;

The medium comprises further compounds from the class of the fluorinated terphenyls where R⁰ and/or X⁰, as defined below, are end groups, preferably selected from the following group consisting of the general formulae XIV and XV:

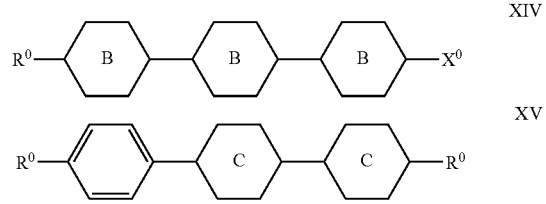

in which

R⁰ denotes n-alkyl, oxaalkyl, fluoroalkyl or alkenyl, each having up to 9 C atoms, X⁰ denotes F, Cl, halogenated alkyl, halogenated alkenyl, halogenated alkenyloxy or halogenated alkoxy having up to 6 C atoms, and rings B and C, independently of one another, denote 1,4-phenylene which is substituted by 0, 1 or 2 fluorine.

In formulae XIV and XV, at least one of the 1,4-phenylene rings is preferably in each case mono- or polysubstituted by fluorine atoms. In compounds of the formula XIV, preferably two of the phenylenes are substituted by at least one fluorine atom or one of the phenylenes is substituted by 2 fluorine atoms; in compounds of the formula XV, one of the phenylenes is preferably substituted by at least one fluorine atom. X⁰ here is preferably F, Cl, CF₃, OCF₃ or OCHF₂. R⁰ here preferably denotes alkyl, alkoxy, oxaalkyl, fluoroalkyl or alkenyl, each having up to 6 C atoms.

Compounds of the formula XIV are preferably compounds of the formulae XIV-1 to XIV-5:

XIV-1
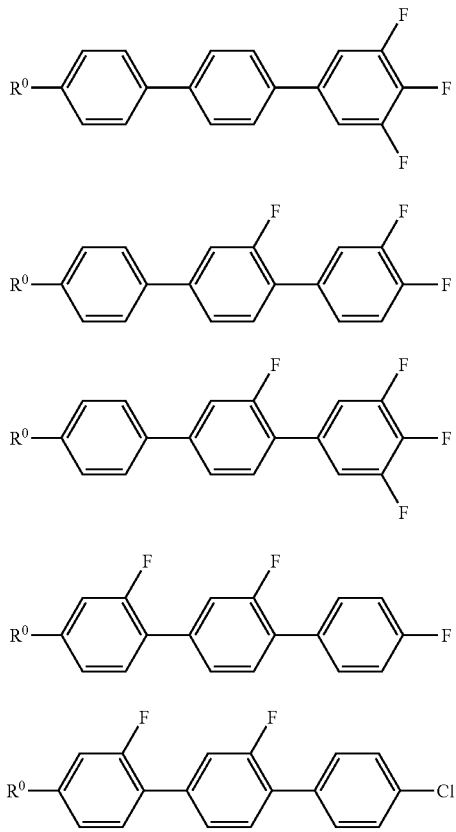
XIV-2

XIV-3

XIV-4

XIV-5 in which $R^0$ is in each case, independently of one another, as defined for the formula XIV.

The proportion of the compounds of the formulae XIV and XV is preferably 0-25% by weight, in particular 2-20% by weight and very particularly 5-15% by weight;

Compounds of the formula XV are preferably a compound of the formula XV-1:

XV-1
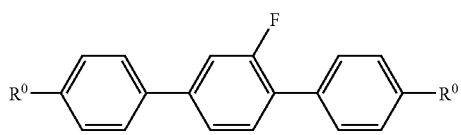

in which $R^0$ is as defined for the formula XV.

The medium comprises further compounds, preferably selected from the following group consisting of the general formulae XVI to XVIII:

XVI
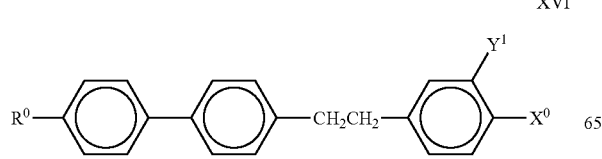

XVII

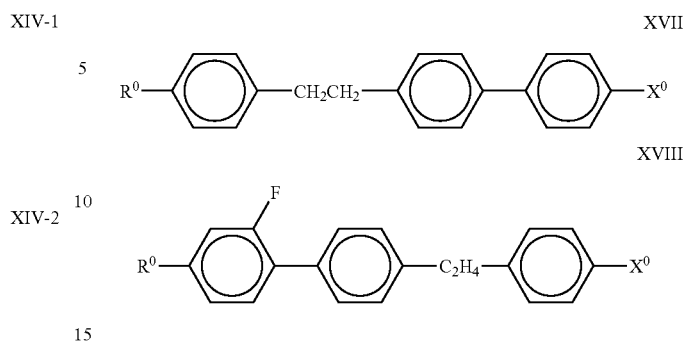

XVIII in which $R^0$ denotes n-alkyl, oxaalkyl, fluoroalkyl or alkenyl, each having up to 9 C atoms, $Y^1$ denotes H or F, and $X^0$ denotes F, Cl, halogenated alkyl, halogenated alkenyl, halogenated alkenyloxy or halogenated alkoxy having up to 6 C atoms;

the 1,4-phenylene rings may additionally be substituted by CN, chlorine or fluorine. The 1,4-phenylene rings are preferably mono- or polysubstituted by fluorine atoms.

The medium additionally comprises one, two, three or more, preferably two or three, compounds of the formulae

O1

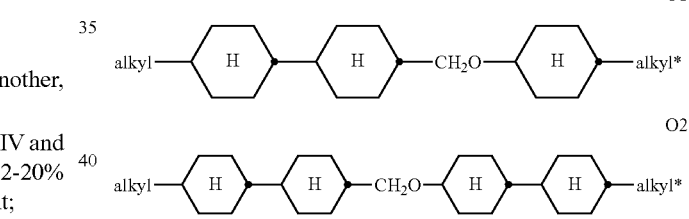

O2 in which "alkyl" and "alkyl*" have the meaning indicated below. The proportion of the compounds of the formulae O1 and/or O2 in the mixtures according to the invention is preferably 0-15% by weight, in particular 1-12% by weight and very particularly preferably 3-10% by weight.

The medium preferably comprises 5-35% by weight of the compound IVa.

The medium preferably comprises one, two or three compounds of the formula IVa in which $X^0$ denotes F or $OCF_3$.

The medium preferably comprises one or more compounds of the formulae IIa to IIg IIa
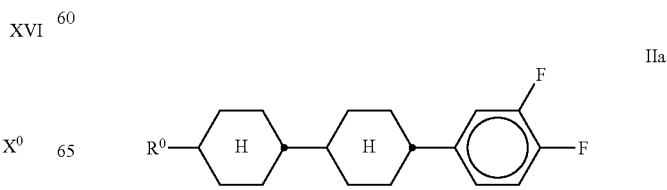

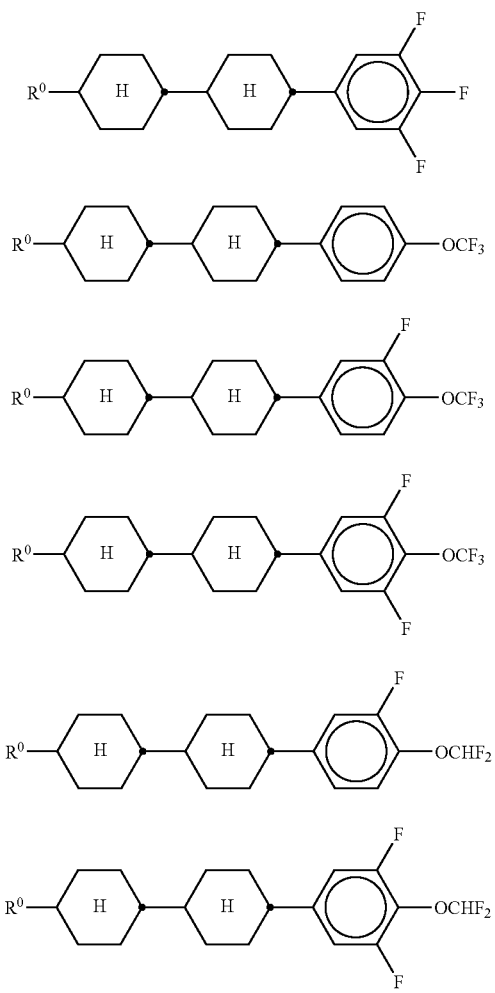
in which
R⁰ denotes n-alkyl, oxaalkyl, fluoroalkyl or alkenyl, each having up to 9 C atoms.
In the compounds of the formulae IIa-IIg, R⁰ preferably denotes methyl, ethyl, n-propyl, n-butyl or n-pentyl.
The medium preferably comprises one or more compounds of the formulae K-1 to K-12 (generally K)
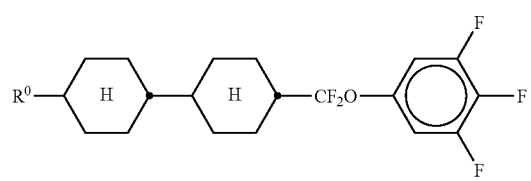
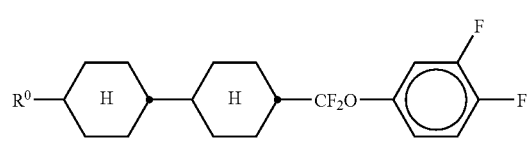
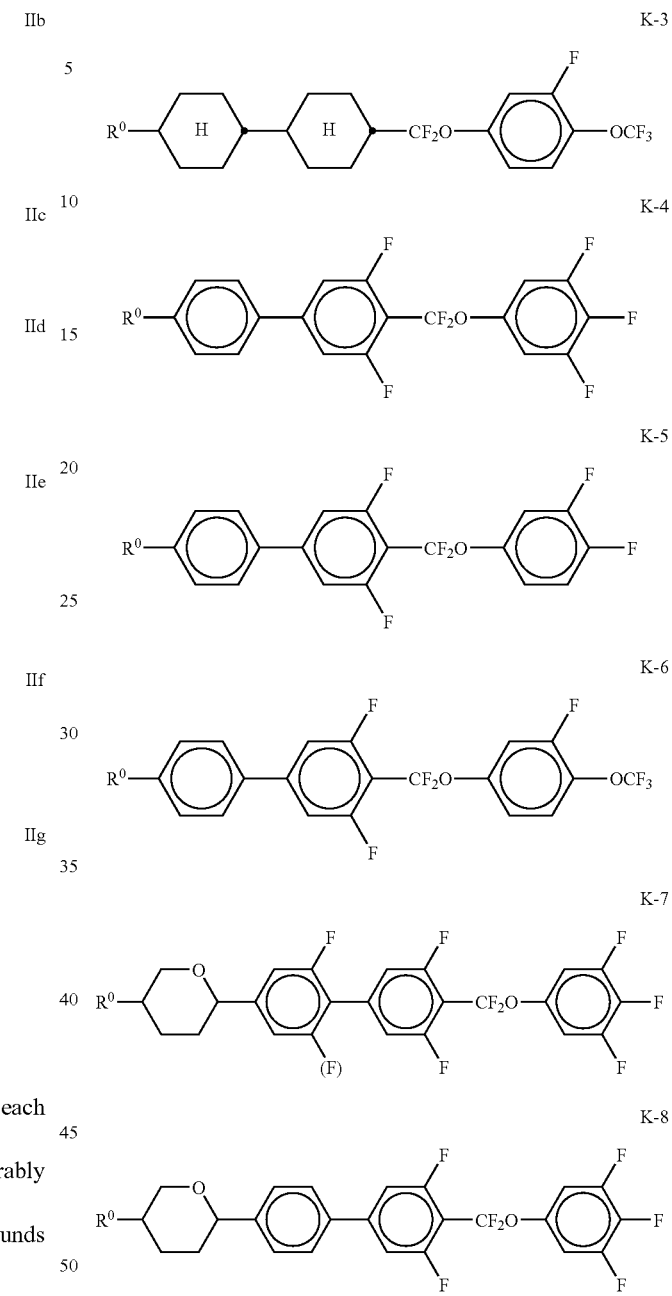

-continued

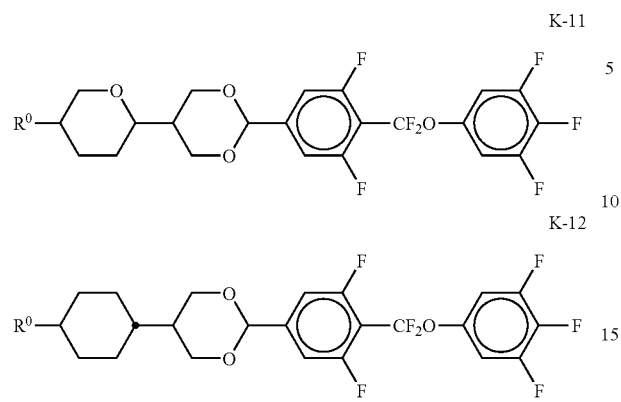

in which
R⁰ denotes n-alkyl, oxaalkyl, fluoroalkyl or alkenyl, each having up to 9 C atoms.

The proportion of compounds of the formulae K (K-1 to K-12) is preferably from 5 to 50% by weight, particularly preferably from 10 to 40% by weight.

The proportion of the compounds of the formulae IVb and/or IVc in which X⁰ denotes fluorine and R⁰ denotes CH₃, C₂H₅, n-C₃H₇, n-C₄H₉ or n-C₅H₁₁ in the mixture as a whole is from 2 to 20% by weight, in particular from 2 to 15% by weight.

The medium preferably comprises compounds of the formulae II to VI in which R⁰ denotes methyl. The medium according to the invention particularly preferably comprises compounds of the formulae

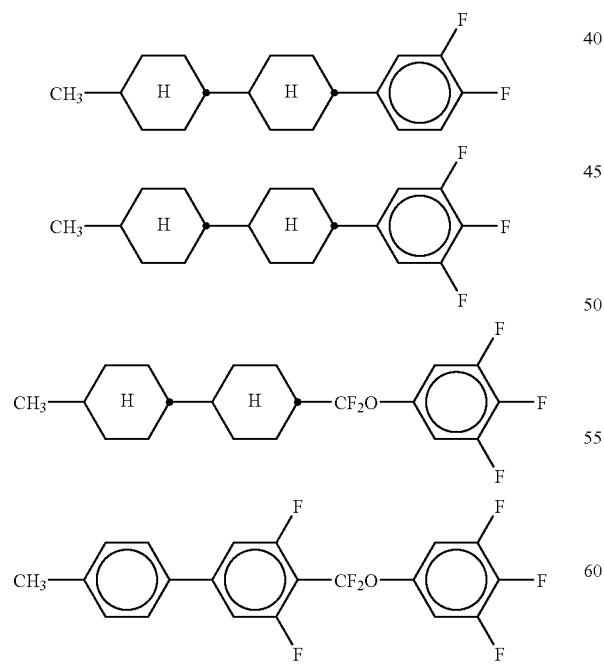

The medium preferably comprises one, two or more, preferably one or two, dioxane compounds of the formulae

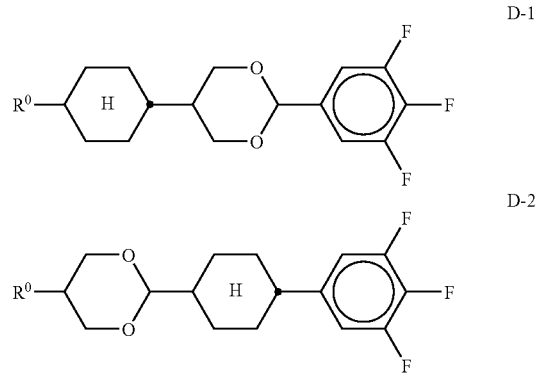

in which
R⁰ denotes n-alkyl, oxaalkyl, fluoroalkyl or alkenyl, each having up to 9 C atoms.

The proportion of the dioxane compounds D-1 and/or D-2 in the mixtures according to the invention is preferably 0-25% by weight, in particular 0-20% by weight and very particularly preferably 0-15% by weight.

The medium preferably comprises one, two or more, preferably one or two, pyran compounds of the formulae P-1 to P-4

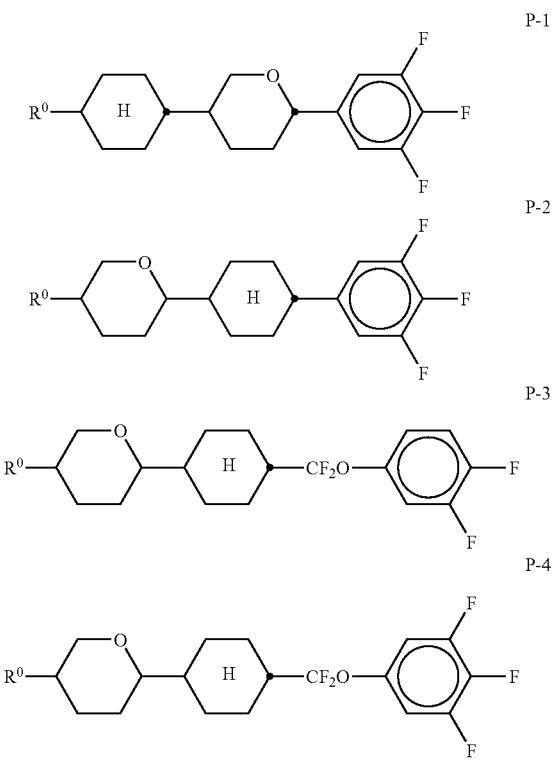

in which
R⁰ denotes n-alkyl, oxaalkyl, fluoroalkyl or alkenyl, each having up to 9 C atoms.

The medium additionally comprises one, two or more bicyclic compounds of the formulae Z-1 to Z-9 (generally Z)

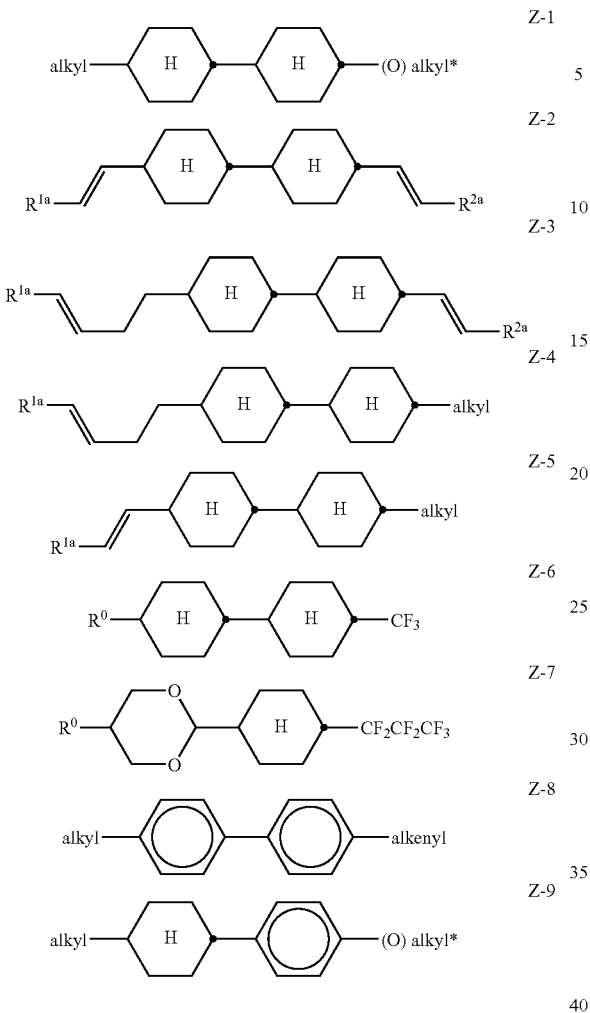

Z-1
Z-2
Z-3
Z-4
Z-5
Z-6
Z-7
Z-8
Z-9 in which

R$^{1a}$ and R$^{2a}$ each, independently of one another, denote H, CH$_3$, C$_2$H$_5$ or n-C$_3$H$_7$, and R$^0$ denotes n-alkyl, oxaalkyl, fluoroalkyl or alkenyl, each having up to 9 C atoms.

Alkyl, alkyl* and alkenyl have the meanings indicated below.

Of the said bicyclic compounds, particular preference is given to the compounds Z-2, Z-5, Z-4 and Z-6, very particularly the compounds of the formula Z-5 where alkyl is propyl and R$^{1a}$ is H or methyl, in particular where R$^{1a}$ is H.

The proportion of compounds of the formulae Z-1 to Z-9 is in total from 5 to 70% by weight, preferably from 15 to 50% by weight. The proportion of compounds of the formula Z-5 alone is preferably from 10 to 60% by weight, preferably from 15 to 50% by weight.

The medium essentially consists of compounds selected from the group consisting of the general formulae I to VI, K-1 to K-12 and from Z-1 to Z-9.

The medium additionally comprises one or more UV-stabilising compounds, in particular a quaterphenyl compound. Particular preference is given to mono- or polyfluorinated quaterphenyl compounds of the formula

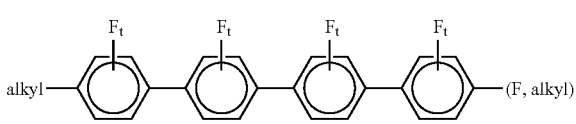

where t is in each case, independently, 0, 1 or 2, and very particularly of the formula

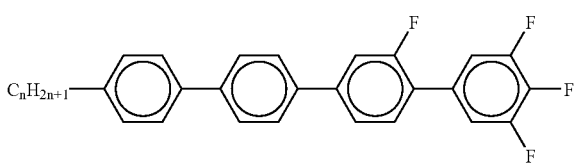

where n is from 1 to 8.

The medium additionally comprises one, two or more compounds having fused rings, of the formulae AN1 to AN11:

AN1
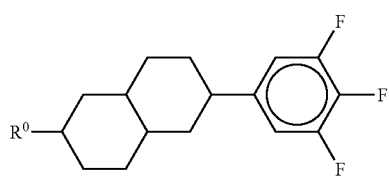

AN2
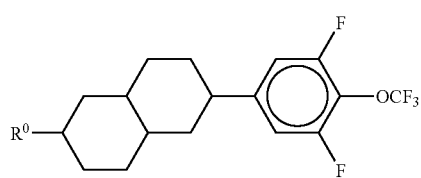

AN3
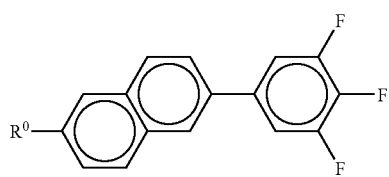

AN4
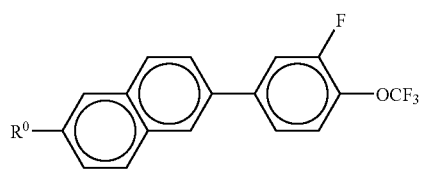

AN5
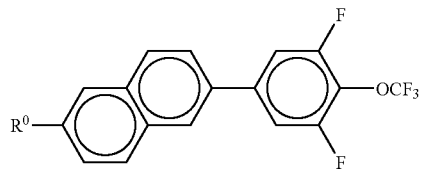

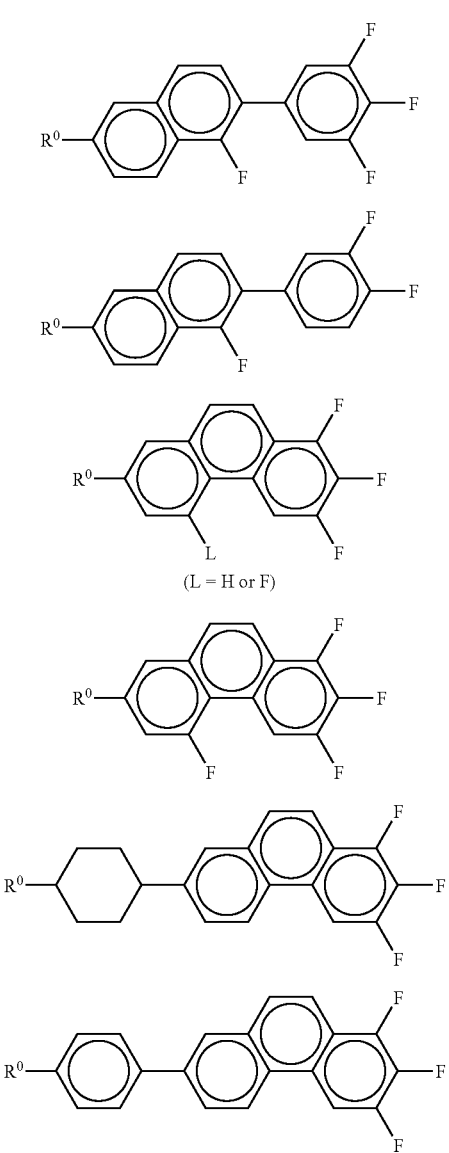

in which R° has the meanings indicated above;

The mixtures according to the invention are distinguished, in particular, by the fact that they have clearing points of ≧70° C. and threshold voltages of <2.0 V.

The mixtures according to the invention are distinguished, in particular, by the fact that they have a dielectric anisotropy of $\Delta \epsilon \geq 3$ and preferably of $\Delta \epsilon > 5$.

It has been found that even a relatively small proportion of compounds of the formula I mixed with conventional liquid-crystal materials, but in particular with one or more compounds of the formulae K, Z. II, III, IV, V and/or VI, results in a significant reduction in the rotational viscosities and response times, with broad nematic phases having low smectic-nematic transition temperatures being observed at the same time, improving the storage stability.

The term "alkyl" or "alkyl*" encompasses straight-chain and branched alkyl groups having 1-7 carbon atoms, in particular the straight-chain groups methyl, ethyl, propyl, butyl, pentyl, hexyl and heptyl. Groups having 1-5 carbon atoms are generally preferred.

The term "alkenyl" encompasses straight-chain and branched alkenyl groups having 2-7 carbon atoms, in particular the straight-chain groups. Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-$C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 204-fluorobutyl, 5-fluoropentyl, 6-fluorohexyl and 7-fluoroheptyl. However, other positions of the fluorine are not excluded.

The term "oxaalkyl" or "alkoxy" preferably encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

Through a suitable choice of the meanings of R° and X°, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

The optimum mixing ratio of the compounds of the formulae I and K+Z+II+III+IV+V+VI depends substantially on the desired properties, on the choice of the components of the formulae I, II, III, IV, V and/or VI, and on the choice of any further components that may be present.

Suitable mixing ratios within the range indicated above can easily be determined from case to case.

The total amount of compounds of the formula I and the co-components indicated in the mixtures according to the invention is not crucial. The mixtures can therefore comprise one or more further components for the purposes of optimisation of various properties. However, the observed effect on the addressing times and the threshold voltage is generally greater, the higher the total concentration of compounds of the formula I and the co-components indicated.

In a particularly preferred embodiment, the media according to the invention comprise compounds of the formulae II to VI (preferably II, III and/or IV, in particular IVa) in which X° denotes F, $OCF_3$, $OCHF_2$, $OCH=CF_2$, $OCF=CF_2$ or $OCF_2$—$CF_2H$. A favourable synergistic effect with the compounds of the formula I results in particularly advantageous properties. In particular, mixtures comprising compounds of the formula I and formula IVa are distinguished by their low threshold voltage.

The individual compounds which can be used in the media according to the invention are either known or can be prepared analogously to the known compounds.

The construction of the MLC display according to the invention from polarisers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

Preferred mixture components are found in Tables A and B.

| Code for $R^{1*}$, $R^{2*}, L^{1*}, L^{2*}, L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| n0m | $OC_nH_{2n+1}$ | $C_mH_{2m+1}$ | H | H |
| n0•m | $C_nH_{2n+1}$ | $OC_mH_{2m+1}$ | H | H |
| n | $C_nH_{2n+1}$ | CN | H | H |
| nN•F | $C_nH_{2n+1}$ | CN | F | H |
| nN•F•F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF•F | $C_nH_{2n+1}$ | F | F | H |
| nF•F•F | $C_nH_{2n+1}$ | F | F | F |
| nmF | $C_nH_{2n+1}$ | $C_mH_{2m+1}$ | F | H |
| nOCF$_3$ | $C_nH_{2n+1}$ | OCF$_3$ | H | H |
| nOCF$_3$•F | $C_nH_{2n+1}$ | OCF$_3$ | F | H |
| nOCF$_3$•F•F | $C_nH_{2n+1}$ | OCF$_3$ | F | F |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

A significant difference between the displays according to the invention and the hitherto conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilisers, such as Tinuvin® from Ciba, antioxidants, free-radical scavengers, etc. For example, 0-15% of pleochroic dyes or chiral dopants can be added. Suitable stabilisers and dopants are mentioned below in Tables C and D.

The threshold voltage $V_{10}$ denotes the voltage for 10% transmission (viewing angle perpendicular to the plate surface). $t_{on}$ denotes the switch-on time and $t_{off}$ the switch-off time at an operating voltage corresponding to 2.0 times the value of $V_{10}$. $\Delta n$ denotes the optical anisotropy. $\Delta \varepsilon$ denotes the dielectric anisotropy ($\Delta \varepsilon = \varepsilon_\| - \varepsilon_\perp$, where $\varepsilon_\|$ denotes the dielectric constant parallel to the longitudinal molecular axes and $\varepsilon_\perp$ denotes the dielectric constant perpendicular thereto). The electro-optical data are measured in a TN cell at the 1st minimum (i.e. at a d·Δn value of 0.5 μm) at 20° C., unless expressly stated otherwise. The optical data are measured at 20° C., unless expressly stated otherwise.

In the present application and in the examples below, the structures of the liquid-crystal compounds are indicated by means of acronyms, the trans-formation into chemical formulae taking place in accordance with Tables A and B below. All radicals $C_nH_{2n+1}$ and $C_mH_{2m+1}$ are straight-chain alkyl radicals having n and m C atoms respectively; n and m are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

TABLE A

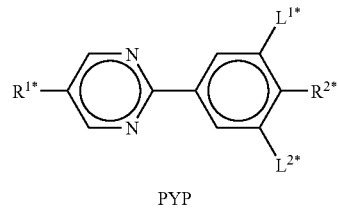

PYP

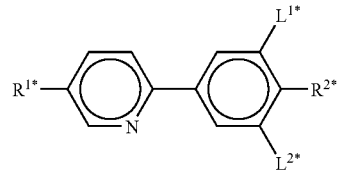

PYRP

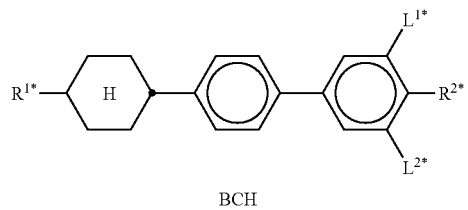

BCH

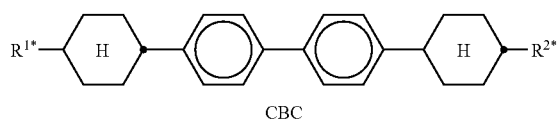

CBC

TABLE A-continued
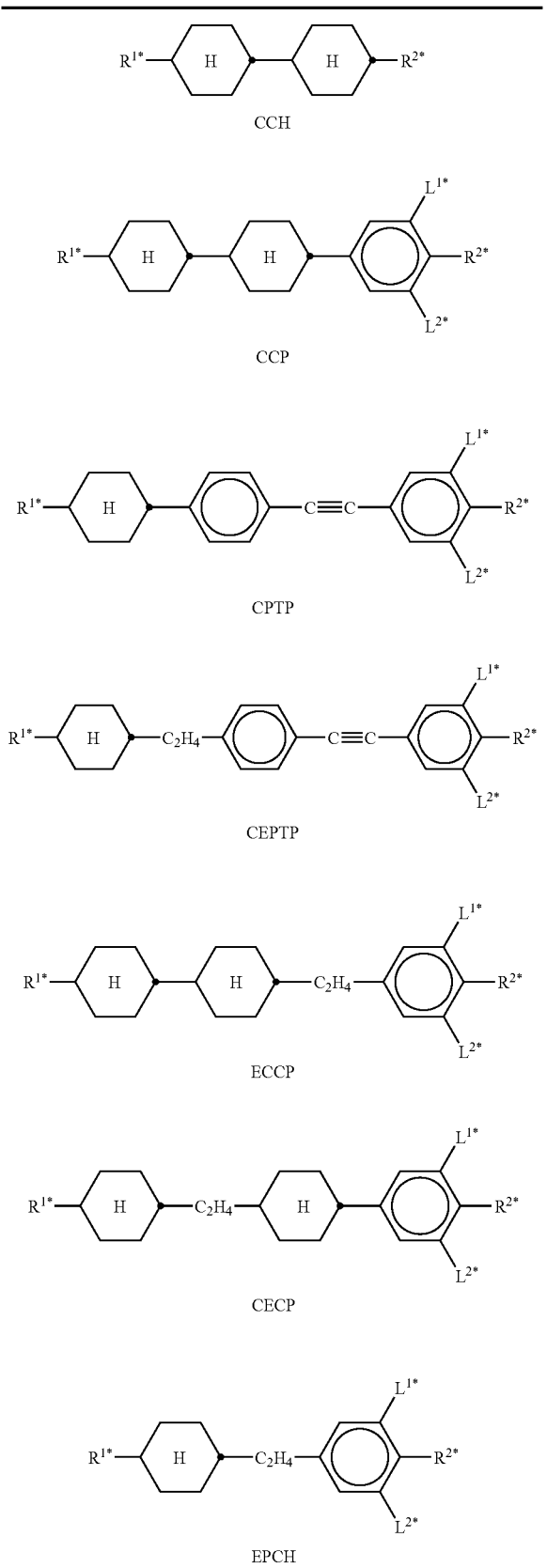
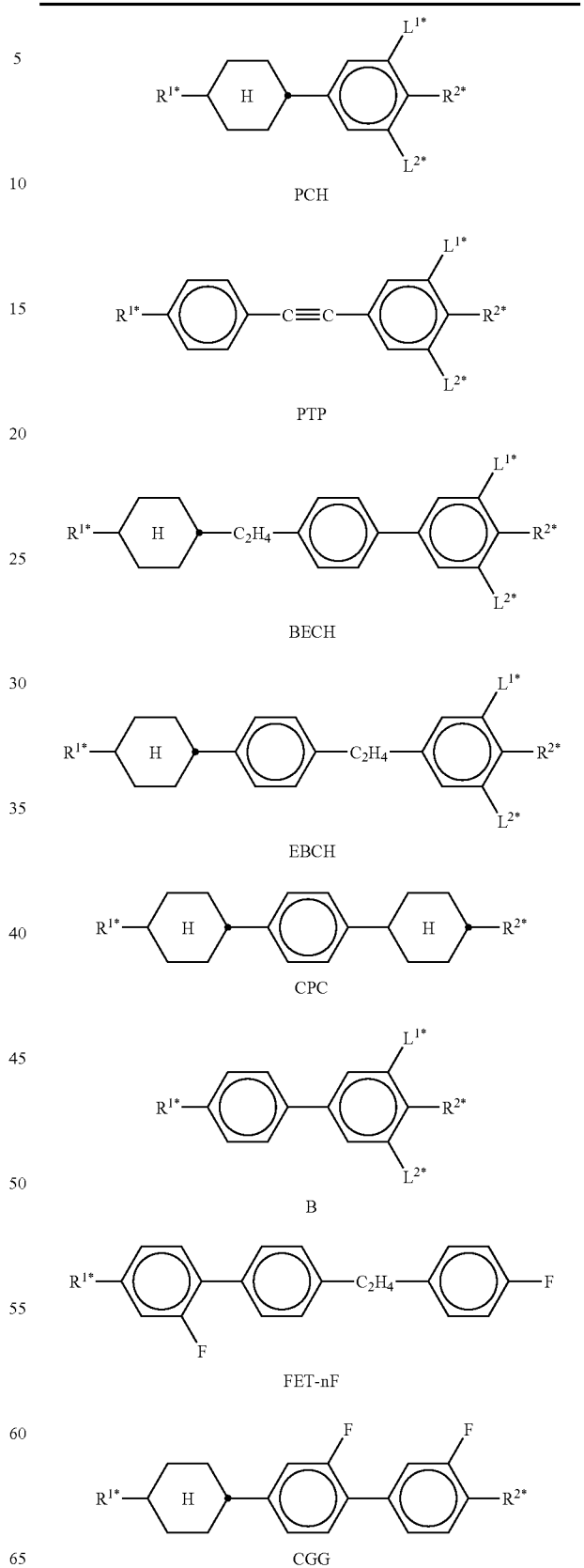

TABLE A-continued
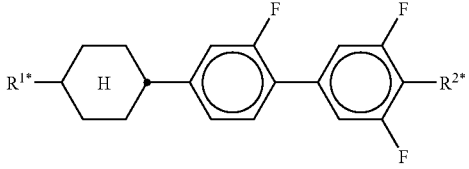
CGU
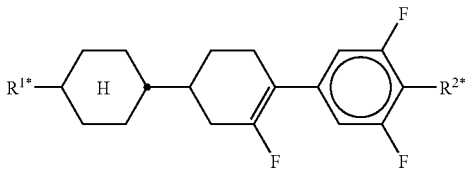
CFU
TABLE B
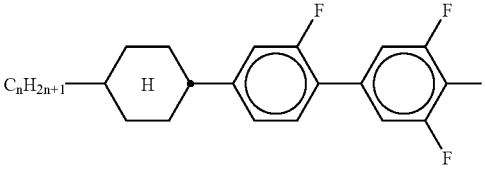
BCH-n·Fm
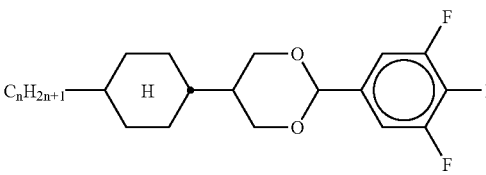
CFU-n-F
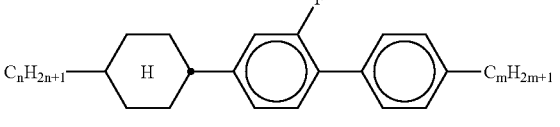
CBC-nmF
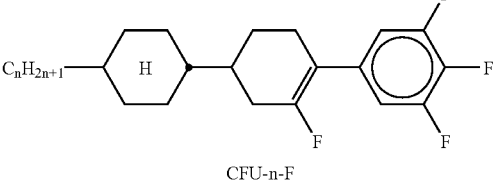
ECCP-nm
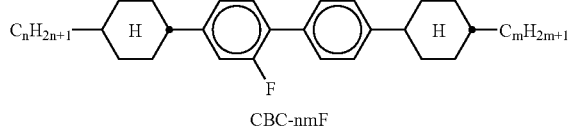
CCZU-n-F
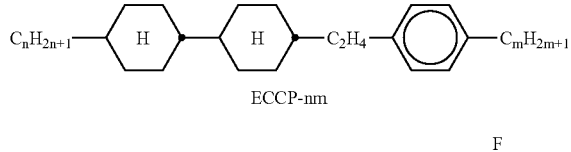
PGP-n-m
TABLE B-continued
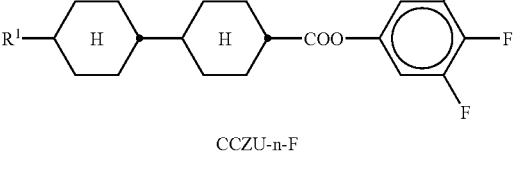
CGU-n-F
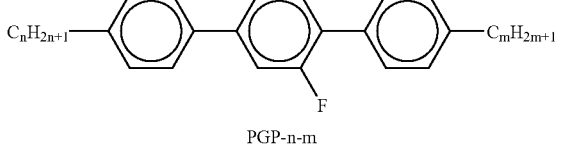
CDU-n-F
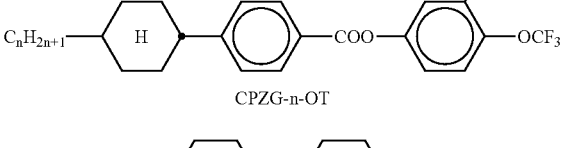
DCU-n-F
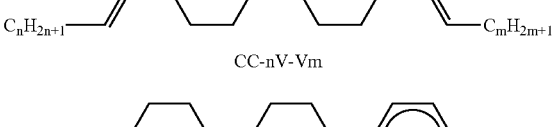
CGG-n-F
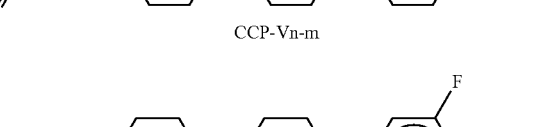
CPZG-n-OT
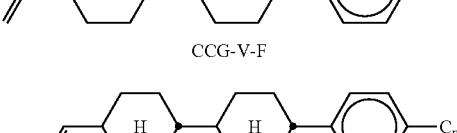
CC-nV-Vm
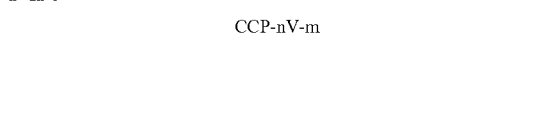
CCP-Vn-m
CCG-V-F
CCP-nV-m TABLE B-continued CCP-V-m CC-n-V CCQU-n-F CC-n-V1

CCQG-n-F

CQCU-n-F

Dec-U-n-F

CWCU-n-F

CWCG-n-F

TABLE B-continued

CCOC-n-m

CPTU-n-F

GPTU-n-F

PQU-n-F

PUQU-n-F

PGU-n-F

PPGU-n-F

CGZP-n-OT

TABLE B-continued

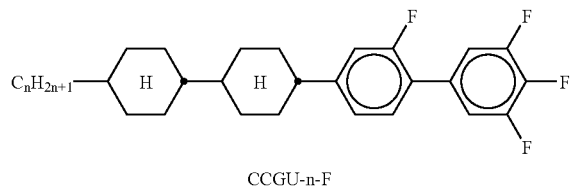

CCGU-n-F

CCQU-n-F

CUQU-n-F

TABLE B-continued

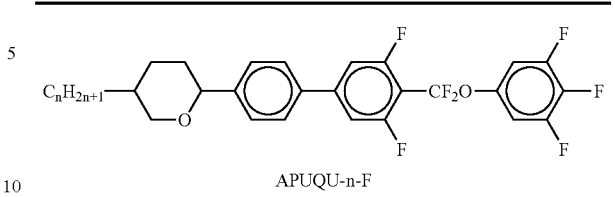

APUQU-n-F

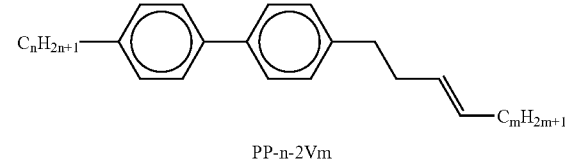

PP-n-2Vm

Particular preference is given to liquid-crystalline mixtures which, besides the compounds of the formula I, comprise at least one, two, three or four compounds from Table B.

TABLE C

Table C indicates possible dopants which are generally added to the mixtures according to the invention. The mixtures preferably comprise 0-10% by weight, in particular 0.01-5% by weight and particularly preferably 0.01-3% by weight of dopants.

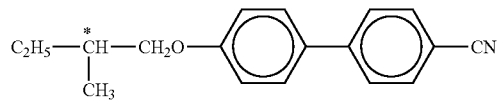

C 15

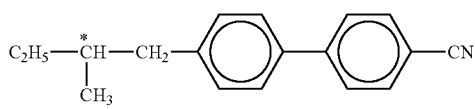

CB 15

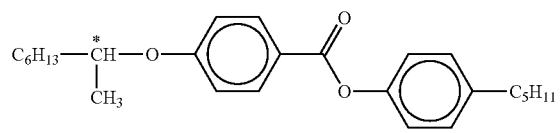

CM 21

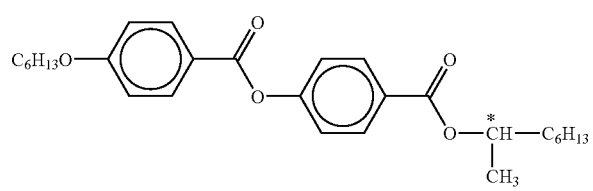

R/S-811

TABLE C-continued
Table C indicates possible dopants which are generally added to the mixtures according to the invention. The mixtures preferably comprise 0-10% by weight, in particular 0.01-5% by weight and particularly preferably 0.01-3% by weight of dopants.
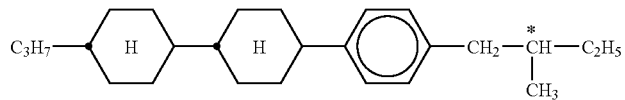
CM 44
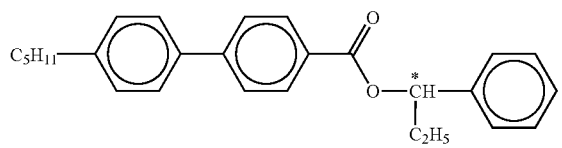
CM 45
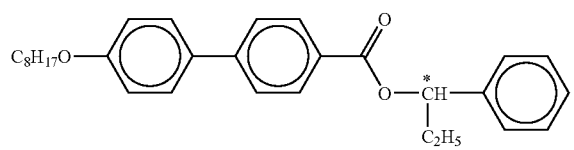
CM 47
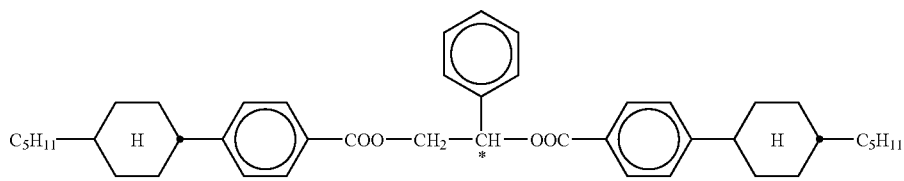
R/S-1011
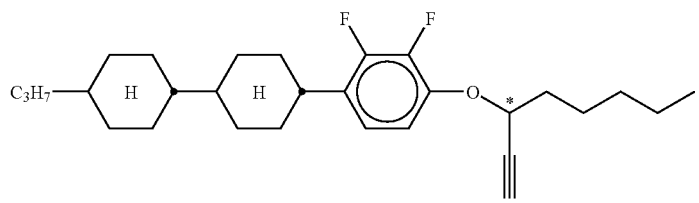
R/S-3011
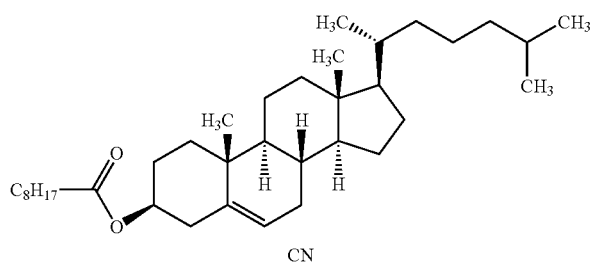
CN
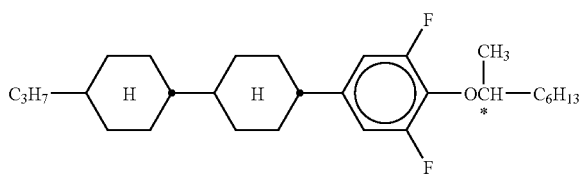
R/S-2011

TABLE C-continued

Table C indicates possible dopants which are generally added to the mixtures according to the invention. The mixtures preferably comprise 0-10% by weight, in particular 0.01-5% by weight and particularly preferably 0.01-3% by weight of dopants.

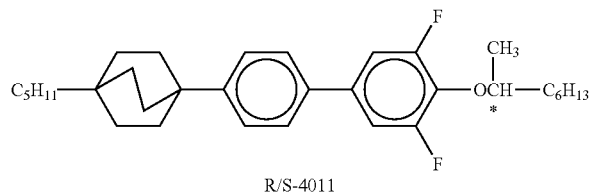

R/S-4011

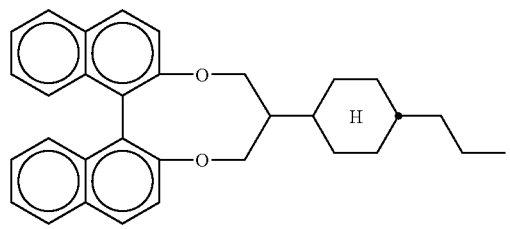

R/S-5011

TABLE D

Stabilisers which can be added, for example, to the mixtures according to the invention are mentioned below.

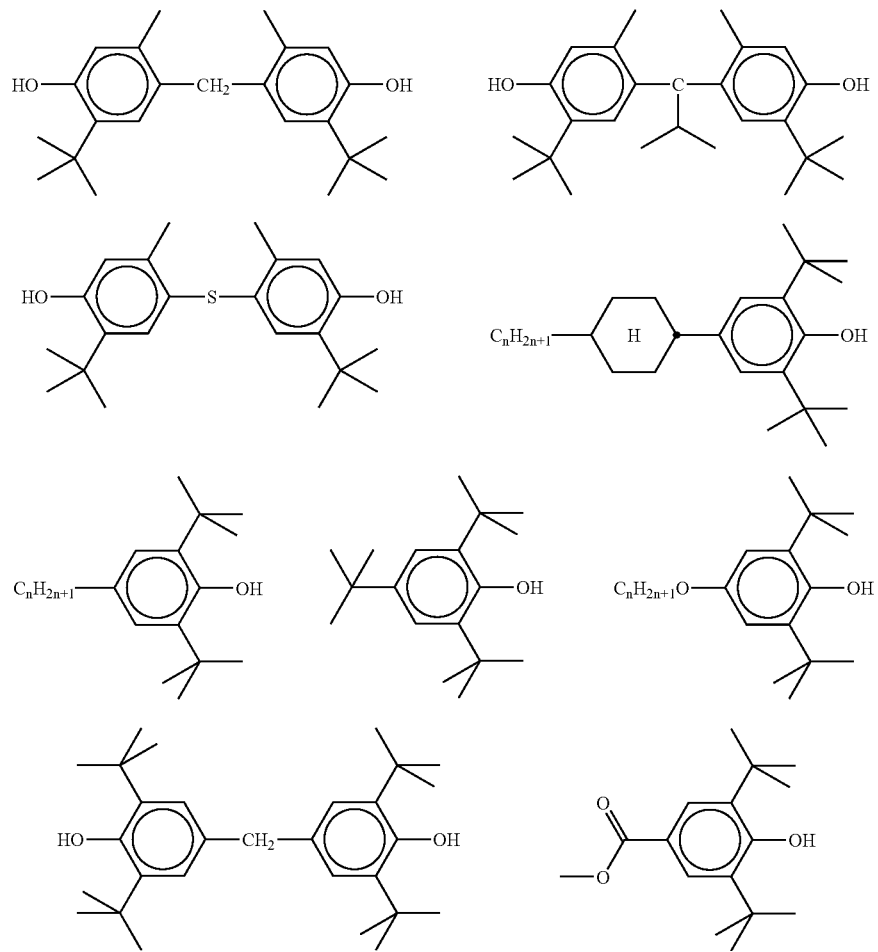

TABLE D-continued
Stabilisers which can be added, for example, to the mixtures according to the invention are mentioned below.
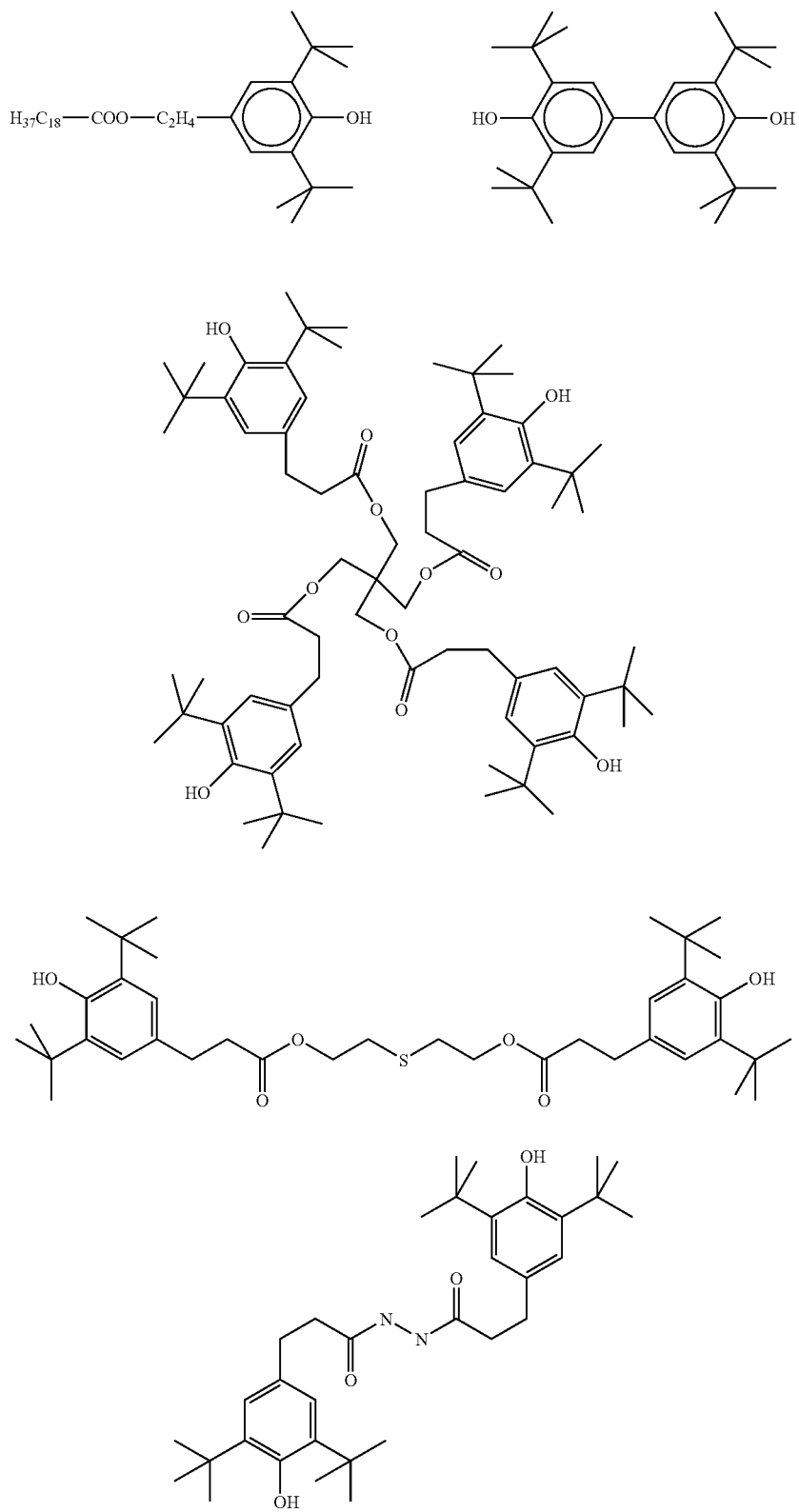

TABLE D-continued
Stabilisers which can be added, for example, to the mixtures according to the invention are mentioned below.
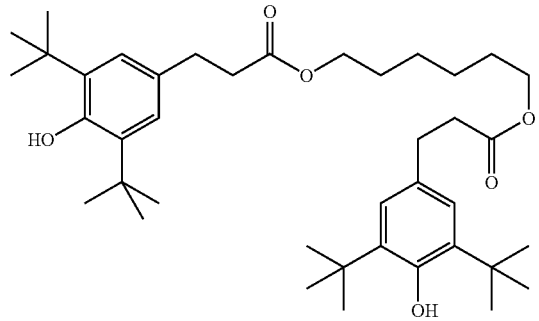
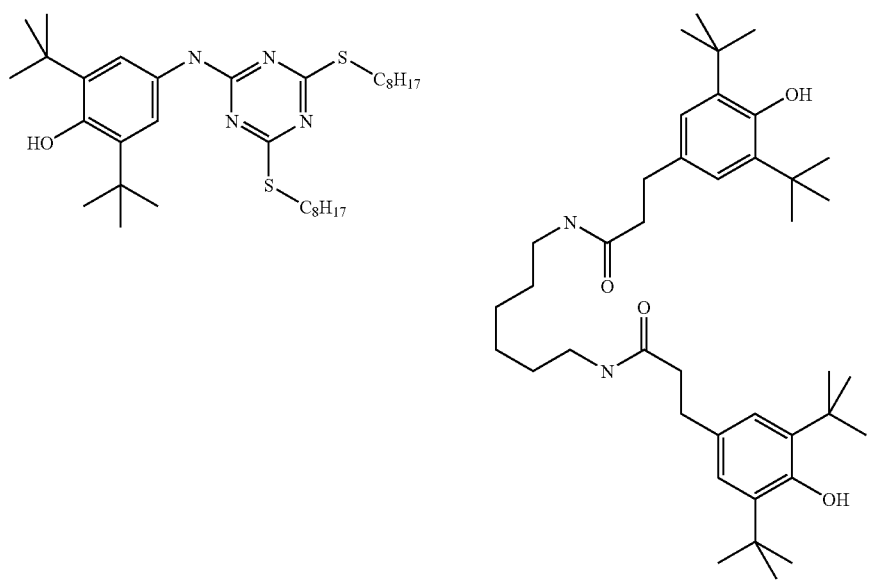
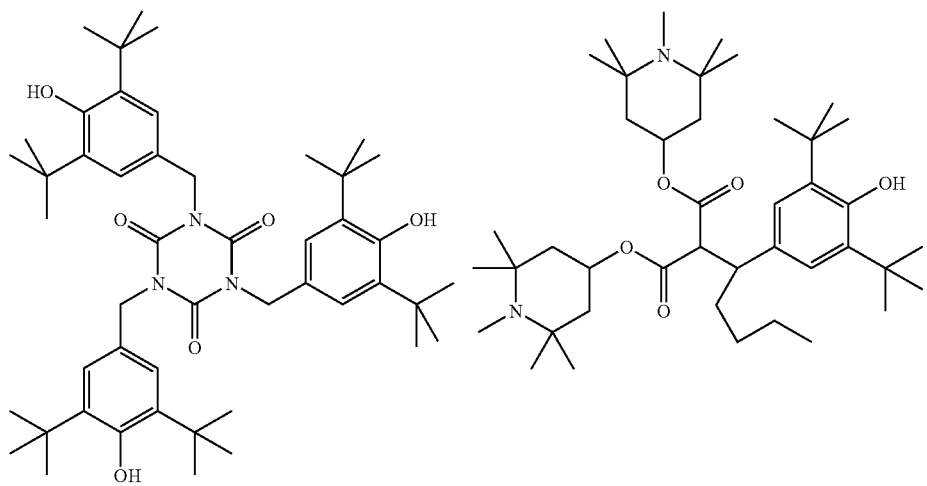

TABLE D-continued
Stabilisers which can be added, for example, to the mixtures according to the invention are mentioned below.
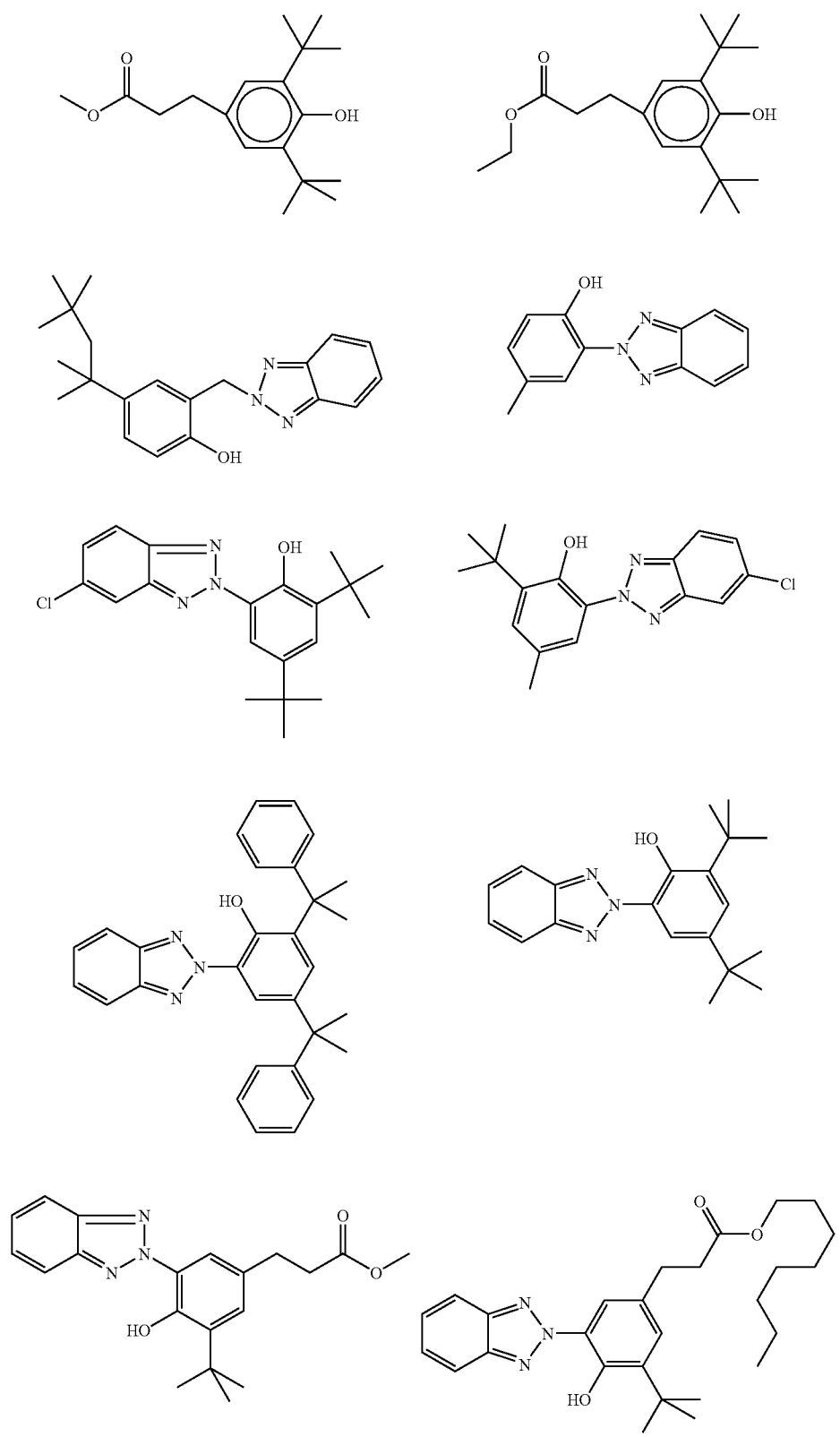

TABLE D-continued

Stabilisers which can be added, for example, to the mixtures according to the invention are mentioned below.

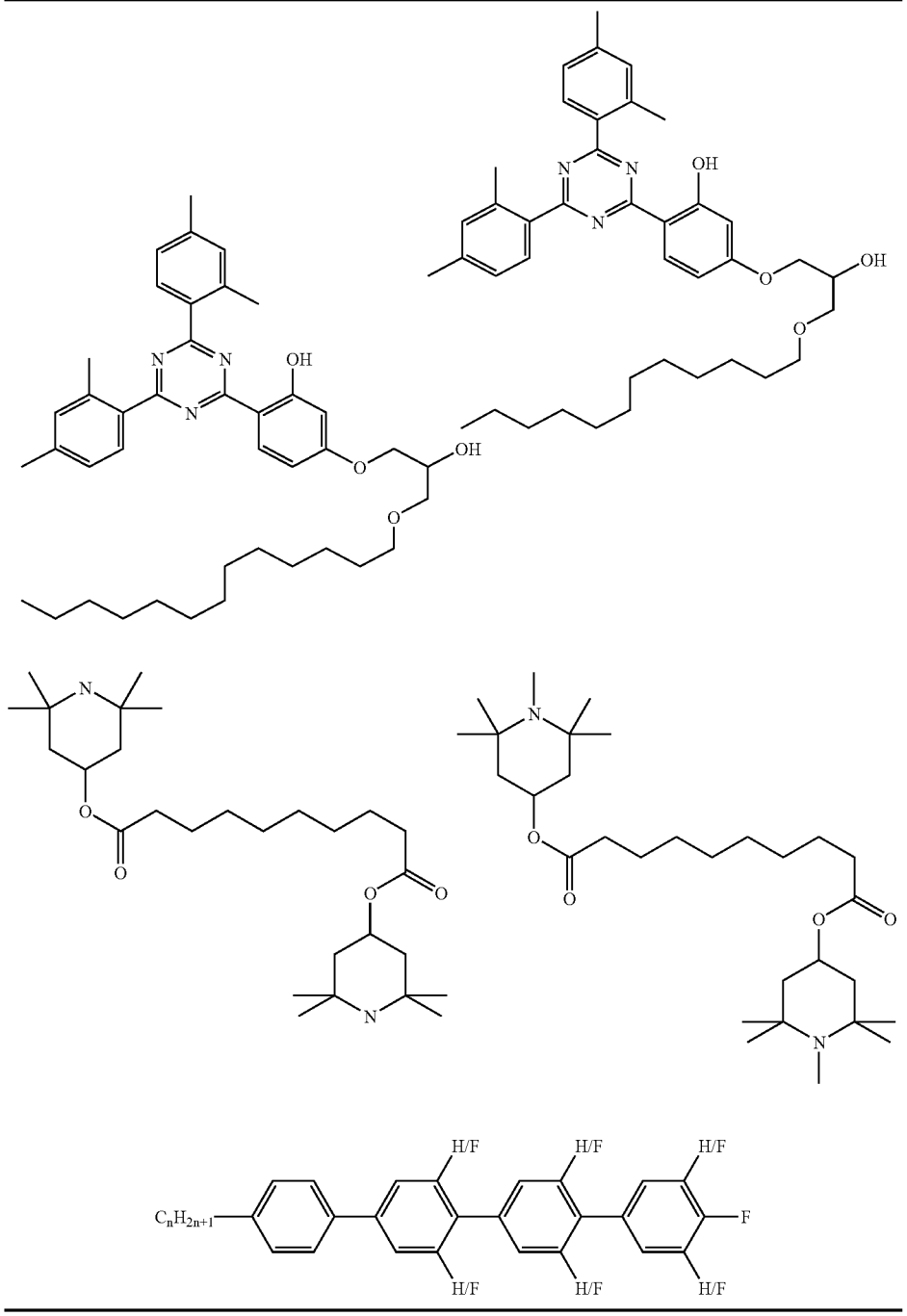

The following examples explain the invention without intending to restrict it. The person skilled in the art will be able to take particularly suitable embodiments, which are not described in greater detail, from the examples and adapt them to different boundary conditions.

Above and below, percentages denote percent by weight. All temperatures are indicated in degrees Celsius. C=crystalline state, N=nematic phase, Sm=smectic phase and I=isotropic phase. The data between these symbols represent the transition temperatures for the pure substances.

The physical measurement methods on mixtures are described in "Merck Liquid Crystals, Physical Properties of Liquid Crystals", November 1997, Merck KGaA.

The dielectric anisotropy $\Delta\epsilon$ of the individual substances is determined at 20° C. and 1 kHz. To this end, 10% by weight of the substances to be investigated are measured dissolved in the dielectrically positive mixture ZLI-4792 (Merck KGaA), and the measurement value is extrapolated to a concentration of 100%. The optical anisotropy $\Delta n$ is determined at 20° C.

and a wavelength of 589.3 nm. It is likewise determined by extrapolation of the values at 10% by weight.

The following abbreviations are used:

clp. clearing point (nematic-isotropic phase transition temperature), $\Delta n$ optical anisotropy (589 nm, 20° C.), $\Delta\epsilon$ dielectric anisotropy (1 kHz, 20° C.), $\epsilon_{\|}-\epsilon_{\perp}$ $\epsilon_{\|}$ proportion of the dielectric constant parallel to the longitudinal molecular axis (1 kHz, 20° C.), $\epsilon_{\perp}$ proportion of the dielectric constant perpendicular to the longitudinal molecular axis (1 kHz, 20° C.), $\gamma_1$ rotational viscosity (20° C.), $t_{store}$ low-temperature storage stability in hours (–20° C., –30° C., –40° C.), $V_{10}$ threshold voltage=characteristic voltage at a relative contrast of 10%, $V_{90}$ saturation voltage=characteristic voltage at a relative contrast of 90%, $k_1$ elastic constant (splay deformation, also $k_{11}$), $k_3$ elastic constant (bend deformation, also $k_{33}$), $k_3/k_1$ ratio of $k_3$ to $k_1$, $V_0$ capacitive or Freederickzs threshold voltage.

SYNTHESIS EXAMPLE 1.1

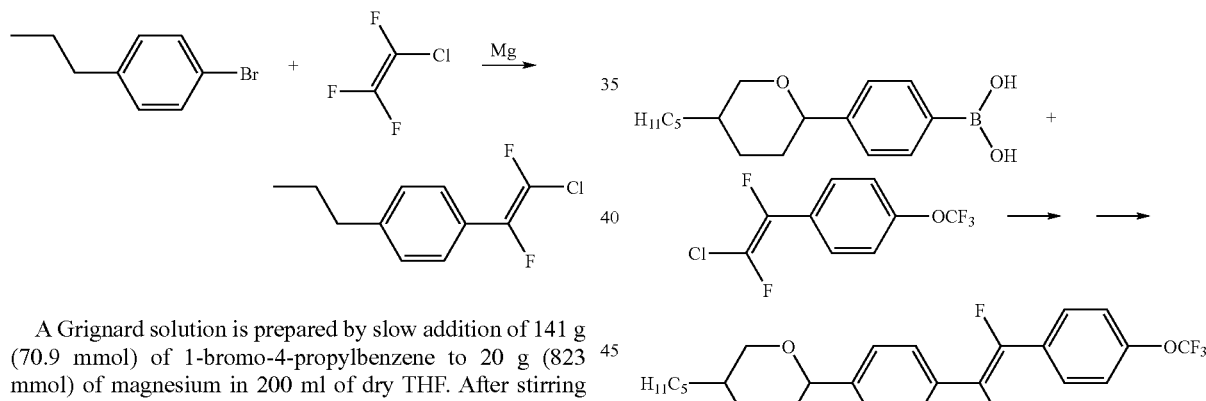

A Grignard solution is prepared by slow addition of 141 g (70.9 mmol) of 1-bromo-4-propylbenzene to 20 g (823 mmol) of magnesium in 200 ml of dry THF. After stirring under reflux for 1 h, the mixture is diluted with 1 l of THF and cooled to –35° C. 100 g (0.86 mol) of chlorotrifluoroethylene are slowly passed in on a dry-ice condenser, and the mixture is stirred for 1.5 h. The reaction solution is warmed to RT, stirred for 12 h and stirred into an ice/2 N HCl mixture. The organic phase is separated off. The aqueous phase is extracted with MTB ether. The combined organic phases are washed with water and NaCl solution, dried and evaporated. The product is a colourless liquid.

SYNTHESIS EXAMPLE 1.2

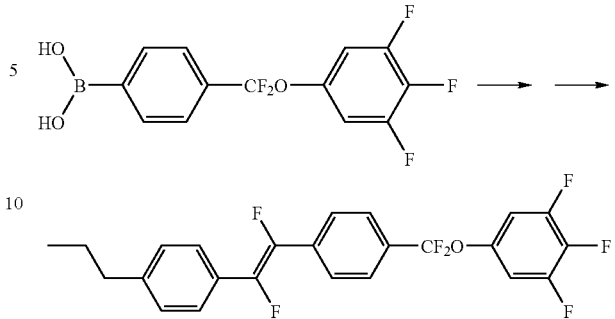

2.02 g (30 mmol) of bis(tricyclohexylphosphine)palladium(II) chloride and 0.154 ml (30 mmol) of hydrazinium hydroxide are added to 18.2 g (97 mmol) of sodium orthosilicate in 50 ml of water under nitrogen, and the mixture is stirred for 5 min. 32.5 g (142 mmol) of the product from Example 1.1 and 50 g (141 mmol) of the boronic acid compound are added, and the mixture is stirred under reflux for 12 h. The organic phase is subsequently separated off, the remainder is washed by shaking, and all organic phases are combined. The purification is carried out by fractionation over 1 l of silica gel using pentane. The product fraction is crystallised from cold isopropanol. Colourless crystals (m.p. 55° C., >99% GC/HPLC). C 55 N 75 I.

SYNTHESIS EXAMPLE 2

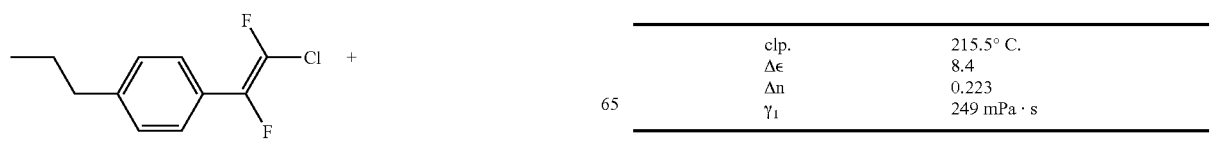

0.40 g (0.72 mmol) of bis(tricyclohexylphosphine)palladium(II) chloride and 0.35 ml (0.72 mmol) of hydrazinium chloride are added to 3.75 g (19.9 mmol) of sodium orthosilicate in 10 ml of water under nitrogen, and the mixture is stirred for 5 min. 7.23 g (28 mmol) of the boronic acid and 7.50 g (27 mmol) of the chlorodifluoroethene compound are added, and the mixture is stirred under reflux for 12 h. After work-up analogously to Example 1.1, the product is crystallised from toluene/methanol (m.p. 39° C., >99% GC/HPLC). C 39 SmB 110 SmA 221 N 226 I.

| | |
|---|---|
| clp. | 215.5° C. |
| $\Delta\epsilon$ | 8.4 |
| $\Delta n$ | 0.223 |
| $\gamma_1$ | 249 mPa · s |

MIXTURE EXAMPLE 1
| | | | |
|---|---|---|---|
| CC-3-V | 26% | Clearing point [° C.]: | 73.5 |
| CC-3-V1 | 7% | Δn [589 nm, 20° C.]: | 0.1007 |
| CCQU-3-F | 12% | Δε [1 kHz, 20° C.]: | +7.8 |
| PUQU-2-F | 9% | γ₁ [mPa · s, 20° C.]: | 57 |
| PUQU-3-F | 12% | $V_{10}$ [V]: | 1.48 |
| CCP-V-1 | 14% | | |
| CCP-30CF3 | 8% | | |
| CCGU-3-F | 3% | | |
| CBC-33 | 1% | | |
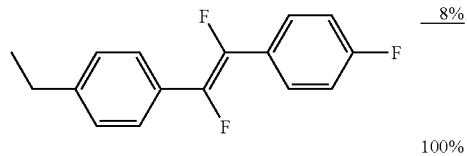
8%
100%
MIXTURE EXAMPLE 2
| | | | |
|---|---|---|---|
| CCP-30CF3 | 4% | Clearing point [° C.]: | 78.0 |
| CCQU-3-F | 12% | Δn [589 nm, 20° C.]: | 0.102 |
| CC-4-V | 14% | Δε [1 kHz, 20° C.]: | +9.7 |
| CC-3-V1 | 14% | γ₁ [mPa · s, 20° C.]: | 72 |
| PUQU-2-F | 14% | $V_{10}$ [V]: | 1.34 |
| PUQU-3-F | 13% | | |
| CCP-V-1 | 20% | | |
| CCGU-3-F | 5% | | |
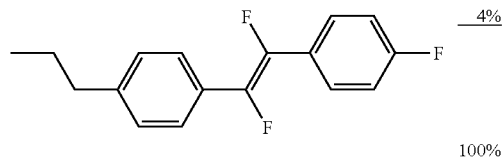
4%
100%
MIXTURE EXAMPLE 3
| | | | |
|---|---|---|---|
| CC-3-V1 | 17% | Clearing point [° C.]: | 76.0 |
| CC-3-V | 31% | Δn [589 nm, 20° C.]: | 0.102 |
| PUQU-2-F | 9% | Δε [1 kHz, 20° C.]: | +5.5 |
| PUQU-3-F | 8% | γ₁ [mPa · s, 20° C.]: | 52 |
| BCH-32 | 4% | $V_{10}$ [V]: | 1.86 |
| CCP-V-1 | 14% | | |
| CCGU-3-F | 9% | | |
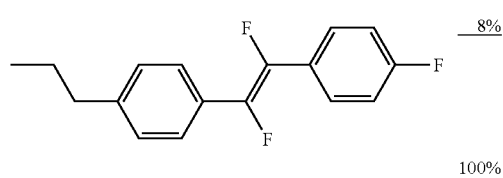
8%
100%

MIXTURE EXAMPLE 4

| | | | |
|---|---|---|---|
| CC-3-V1 | 17% | Clearing point [° C.]: | 76 |
| CC-3-V | 31% | $\Delta n$ [589 nm, 20° C.]: | 0.1023 |
| PUQU-2-F | 9% | $\Delta\epsilon$ [1 kHz, 20° C.]: | +5.5 |
| PUQU-3-F | 8% | $\gamma_1$ [mPa · s, 20° C.]: | 52 |
| BCH-32 | 4% | $V_{10}$ [V]: | 1.86 |
| CCP-V-1 | 14% | | |
| CCGU-3-F | 9% | | |

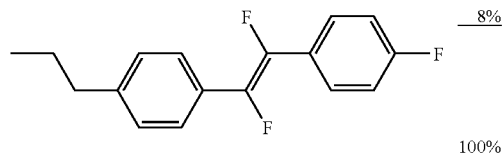

8%

100%

MIXTURE EXAMPLE 5

| | | | |
|---|---|---|---|
| CC-3-V1 | 15% | Clearing point [° C.]: | 75.5 |
| CC-3-V | 31% | $\Delta n$ [589 nm, 20° C.]: | 0.1066 |
| PUQU-2-F | 8% | $\Delta\epsilon$ [1 kHz, 20° C.]: | +5.3 |
| PUQU-3-F | 8% | $\gamma_1$ [mPa · s, 20° C.]: | 49 |
| BCH-32 | 8% | $V_{10}$ [V]: | 1.90 |
| CCP-V-1 | 11% | | |
| CCGU-3-F | 8% | | |
| PP-1-2V1 | 3% | | |

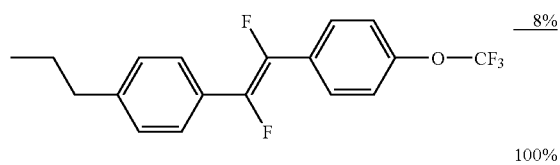

8%

100%

MIXTURE EXAMPLE 6

| | | | |
|---|---|---|---|
| PUQU-2-F | 7% | Clearing point [° C.]: | 77.5 |
| PUQU-3-F | 10% | $\Delta n$ [589 nm, 20° C.]: | 0.1158 |
| CC-3-V | 36% | $\Delta\epsilon$ [1 kHz, 20° C.]: | +7.1 |
| CCP-V-1 | 15% | $\gamma_1$ [mPa · s, 20° C.]: | 57 |
| CCGU-3-F | 8% | $V_{10}$ [V]: | 1.60 |
| BCH-32 | 10% | | |
| PGU-3-F | 6% | | |

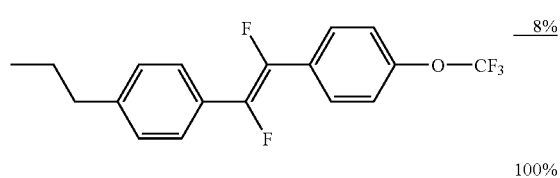

8%

100%

MIXTURE EXAMPLE 7

| | | | |
|---|---|---|---|
| CC-3-V1 | 18% | Clearing point [° C.]: | 75 |
| CC-3-V | 31% | $\Delta n$ [589 nm, 20° C.]: | 0.1082 |
| PUQU-2-F | 8% | $\Delta\epsilon$ [1 kHz, 20° C.]: | +5.5 |
| PUQU-3-F | 11% | $\gamma_1$ [mPa · s, 20° C.]: | 50 |
| BCH-32 | 10% | $V_{10}$ [V]: | 1.82 |
| CCP-V-1 | 6% | | |
| CCGU-3-F | 8% | | |

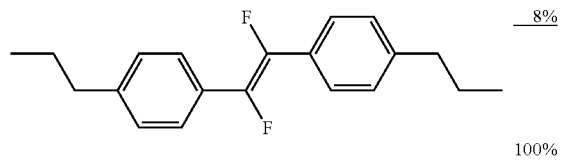

8%

100%

MIXTURE EXAMPLE 8

| | | | |
|---|---|---|---|
| PUQU-3-F | 18% | Clearing point [° C.]: | 75.5 |
| CC-3-V | 31% | $\Delta n$ [589 nm, 20° C.]: | 0.1090 |
| CC-3-V1 | 10% | $\Delta\epsilon$ [1 kHz, 20° C.]: | +7.0 |
| CCP-V-1 | 8% | $\gamma_1$ [mPa · s, 20° C.]: | 57 |
| CCGU-3-F | 8% | $V_{10}$ [V]: | 1.65 |
| BCH-32 | 10% | | |
| PGU-3-F | 7% | | |

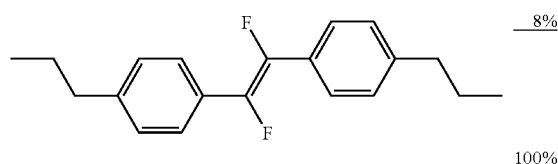

8%

100%

MIXTURE EXAMPLE 9

| | | | |
|---|---|---|---|
| PUQU-3-F | 16% | Clearing point [° C.]: | 75.5 |
| CC-3-V | 43% | $\Delta n$ [589 nm, 20° C.]: | 0.1226 |
| CCGU-3-F | 7% | $\Delta\epsilon$ [1 kHz, 20° C.]: | +7.1 |
| BCH-32 | 6% | $\gamma_1$ [mPa · s, 20° C.]: | 56 |
| APUQU-3-F | 6% | $V_{10}$ [V]: | 1.66 |
| PGP-2-4 | 7% | | |
| PGP-2-3 | 4% | | |
| CBC-33 | 3% | | |

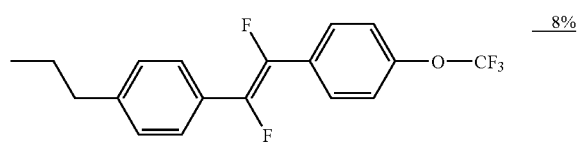

8%

100%

MIXTURE EXAMPLE 10

| | | | |
|---|---|---|---|
| PUQU-3-F | 16% | Clearing point [° C.]: | 74.5 |
| CC-3-V | 43.5% | Δn [589 nm, 20° C.]: | 0.1201 |
| CCGU-3-F | 9% | Δε [1 kHz, 20° C.]: | +7.1 |
| BCH-32 | 5.5% | $\gamma_1$ [mPa · s, 20° C.]: | 57 |
| APUQU-3-F | 6% | $V_{10}$ [V]: | 1.64 |
| PGP-2-4 | 5% | | |
| PGP-2-3 | 4% | | |
| CBC-33 | 3% | | |

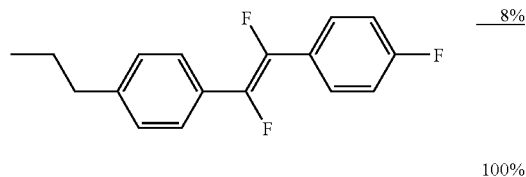

8%

100%

MIXTURE EXAMPLE 11

| | | | |
|---|---|---|---|
| PUQU-3-F | 10% | Clearing point [° C.]: | 75 |
| CC-3-V | 43% | Δn [589 nm, 20° C.]: | 0.1084 |
| CC-3-V1 | 13% | Δε [1 kHz, 20° C.]: | +5.3 |
| CCGU-3-F | 7% | $\gamma_1$ [mPa · s, 20° C.]: | 48 |
| APUQU-3-F | 6% | $V_{10}$ [V]: | 1.88 |
| PGP-2-4 | 6% | | |
| PGP-2-3 | 4% | | |
| CBC-33 | 3% | | |

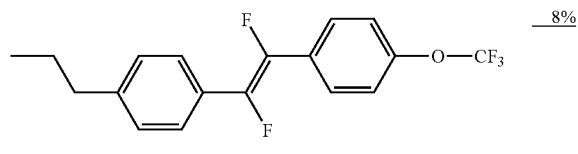

8%

100%

MIXTURE EXAMPLE 12

| | | | |
|---|---|---|---|
| CC-3-V | 40% | Clearing point [° C.]: | 74.5 |
| CC-3-V1 | 11% | Δn [589 nm, 20° C.]: | 0.1187 |
| PUQU-3-F | 3% | Δε [1 kHz, 20° C.]: | +4.6 |
| PGU-2-F | 7% | $\gamma_1$ [mPa · s, 20° C.]: | 49 |
| PGU-3-F | 10% | $V_{10}$ [V]: | 1.94 |
| PGP-2-3 | 5% | | |
| PGP-2-4 | 3.5% | | |
| CCP-30CF3 | 2% | | |
| CCP-V-1 | 6.5% | | |
| CCGU-3-F | 3% | | |
| CBC-33 | 3% | | |

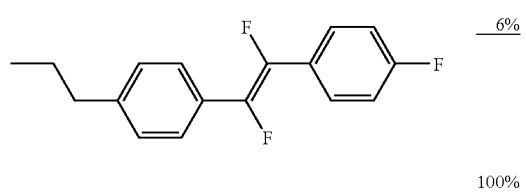

6%

100%

MIXTURE EXAMPLE 13

| | | | |
|---|---|---|---|
| PUQU-3-F | 17% | Clearing point [° C.]: | 76 |
| CC-3-V | 37% | Δn [589 nm, 20° C.]: | 0.1193 |
| CC-3-V1 | 5% | Δε [1 kHz, 20° C.]: | +7.3 |
| CCP-V-1 | 6% | $\gamma_1$ [mPa · s, 20° C.]: | 56 |
| CCGU-3-F | 8% | $V_{10}$ [V]: | 1.64 |
| BCH-32 | 10% | | |
| PGU-3-F | 5% | | |
| PPGU-4-F | 3% | | |
| PGP-2-3 | 3% | | |

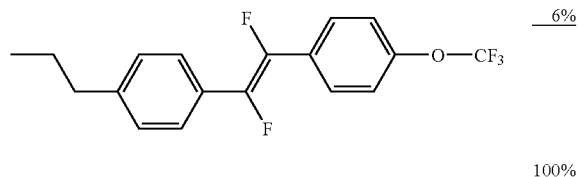

6%

100%

MIXTURE EXAMPLE 14

| | | | |
|---|---|---|---|
| CC-3-V1 | 15% | Clearing point [° C.]: | 76 |
| CC-3-V | 36% | Δn [589 nm, 20° C.]: | 0.1092 |
| PUQU-3-F | 16% | Δε [1 kHz, 20° C.]: | +5.6 |
| BCH-32 | 10% | $\gamma_1$ [mPa · s, 20° C.]: | 51 |
| CCP-V-1 | 4% | $V_{10}$ [V]: | 1.87 |
| CCGU-3-F | 7% | | |
| PPGU-4-F | 3% | | |
| PGP-2-4 | 3% | | |

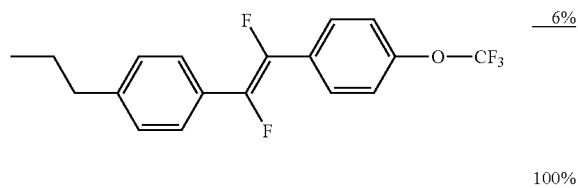

6%

100%

MIXTURE EXAMPLE 15

| | | | |
|---|---|---|---|
| PUQU-3-F | 17% | Clearing point [° C.]: | 75 |
| CC-3-V | 38% | Δn [589 nm, 20° C.]: | 0.1184 |
| CCP-V-1 | 9% | Δε [1 kHz, 20° C.]: | +7.0 |
| CCGU-3-F | 10% | $\gamma_1$ [mPa · s, 20° C.]: | 58 |
| BCH-32 | 10% | $V_{10}$ [V]: | 1.65 |
| PGU-3-F | 6% | | |
| PGP-2-4 | 4% | | |

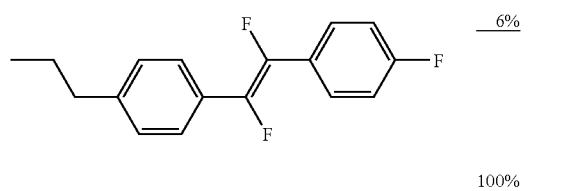

6%

100%

MIXTURE EXAMPLE 16

| | | | |
|---|---|---|---|
| PGU-2-F | 5% | Clearing point [° C.]: | 75.0 |
| CDU-2-F | 6% | Δn [589 nm, 20° C.]: | 0.0972 |
| CCZU-3-F | 15% | Δε [1 kHz, 20° C.]: | +8.5 |
| CC-3-V1 | 13% | $\gamma_1$ [mPa · s, 20° C.]: | 61 |
| CC-3-V | 21% | $k_1$ [pN, 20° C.] | 13.1 |
| CCP-V-1 | 6% | $k_3/k_1$ [pN, 20° C.] | 0.95 |
| CCP-30CF3 | 8% | $V_0$ [V, 20° C.] | 1.30 |
| CCP-40CF3 | 6% | | |
| PUQU-2-F | 7% | | |
| PUQU-3-F | 7% | | |
| | 6% | | |
| | 100% | | |

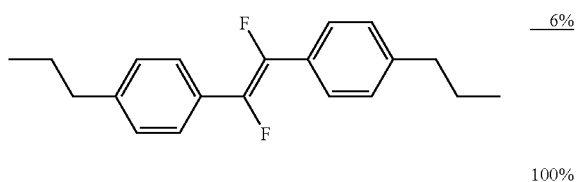

MIXTURE EXAMPLE 17

| | | | |
|---|---|---|---|
| PGU-2-F | 6.5% | Clearing point [° C.]: | 75.5 |
| CDU-2-F | 4.5% | Δn [589 nm, 20° C.]: | 0.0976 |
| CCZU-3-F | 12% | Δε [1 kHz, 20° C.]: | +8.4 |
| CC-3-V1 | 13% | $\gamma_1$ [mPa · s, 20° C.]: | 61 |
| CC-3-V | 21% | $k_1$ [pN, 20° C.] | 12.6 |
| CCP-V-1 | 8% | $k_3/k_1$ [pN, 20° C.] | 1.02 |
| CCP-30CF3 | 8% | $V_0$ [V, 20° C.] | 1.29 |
| CCP-40CF3 | 8% | | |
| PUQU-2-F | 7% | | |
| PUQU-3-F | 6% | | |
| | 6% | | |
| | 100% | | |

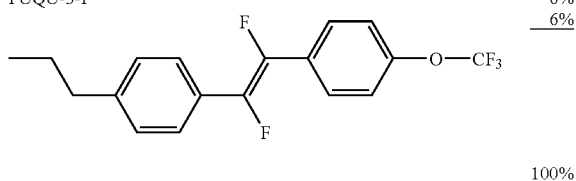

MIXTURE EXAMPLE 18

| | | | |
|---|---|---|---|
| CC-3-V | 19% | Clearing point [° C.]: | 75.5 |
| CC-3-V1 | 13% | Δn [589 nm, 20° C.]: | 0.0975 |
| CCP-30CF3 | 8% | Δε [1 kHz, 20° C.]: | +8.6 |
| CCP-40CF3 | 8% | $\gamma_1$ [mPa · s, 20° C.]: | 65 |
| CCP-V-1 | 8% | $k_1$ [pN, 20° C.] | 12.5 |
| CCZU-3-F | 13% | $k_3/k_1$ [pN, 20° C.] | 1.01 |
| CDU-2-F | 6.5% | $V_0$ [V, 20° C.] | 1.27 |
| PGU-2-F | 5.5% | | |
| PUQU-2-F | 7% | | |
| PUQU-3-F | 6% | | |
| | 6% | | |
| | 100% | | |

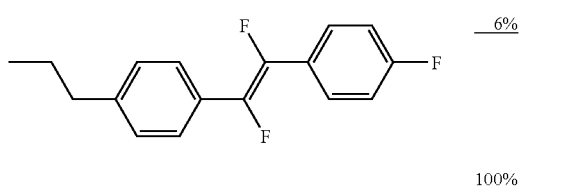

MIXTURE EXAMPLE 19

| | | | |
|---|---|---|---|
| CC-3-V | 13% | Clearing point [° C.]: | 78.5 |
| CC-3-V1 | 12% | Δn [589 nm, 20° C.]: | 0.1105 |
| CCGU-3-F | 5% | Δε [1 kHz, 20° C.]: | +11.4 |
| CCP-30CF3 | 8% | $\gamma_1$ [mPa·s, 20° C.]: | 78 |
| CCP-V-1 | 10.5% | $k_1$ [pN, 20° C.] | 13.0 |
| CCZU-3-F | 12% | $k_3/k_1$ [pN, 20° C.] | 0.98 |
| CDU-2-F | 9% | $V_0$ [V, 20° C.] | 1.12 |
| PGU-2-F | 7.5% | | |
| PUQU-2-F | 8.5% | | |
| PUQU-3-F | 8.5% | | |
| | 6% | | |
| | 100% | | |

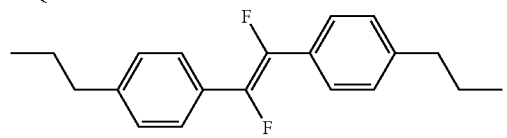

MIXTURE EXAMPLE 20

| | | | |
|---|---|---|---|
| CC-3-V | 14.5% | Clearing point [° C.]: | 79.0 |
| CC-3-V1 | 12% | Δn [589 nm, 20° C.]: | 0.1097 |
| CCGU-3-F | 7% | Δε [1 kHz, 20° C.]: | +11.3 |
| CCP-30CF3 | 7% | $\gamma_1$ [mPa·s, 20° C.]: | 78 |
| CCP-V-1 | 12.5% | $k_1$ [pN, 20° C.] | 12.4 |
| CCZU-3-F | 9% | $k_3/k_1$ [pN, 20° C.] | 1.06 |
| CDU-2-F | 7% | $V_0$ [V, 20° C.] | 1.10 |
| PGU-2-F | 8% | | |
| PUQU-2-F | 8.5% | | |
| PUQU-3-F | 8.5% | | |
| | 6% | | |
| | 100% | | |

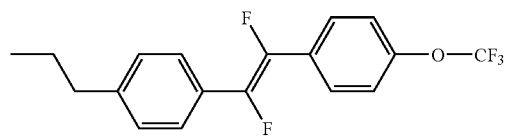

MIXTURE EXAMPLE 21

| | | | |
|---|---|---|---|
| CC-3-V | 12.5% | Clearing point [° C.]: | 79 |
| CC-3-V1 | 12% | Δn [589 nm, 20° C.]: | 0.1100 |
| CCGU-3-F | 7% | Δε [1 kHz, 20° C.]: | +11.4 |
| CCP-30CF3 | 8% | $\gamma_1$ [mPa·s, 20° C.]: | 81 |
| CCP-V-1 | 12.5% | $k_1$ [pN, 20° C.] | 12.2 |
| CCZU-3-F | 9% | $k_3/k_1$ [pN, 20° C.] | 1.07 |
| CDU-2-F | 9% | $V_0$ [V, 20° C.] | 1.09 |
| PGU-2-F | 7% | | |
| PUQU-2-F | 8.5% | | |
| PUQU-3-F | 8.5% | | |
| | 6% | | |
| | 100% | | |

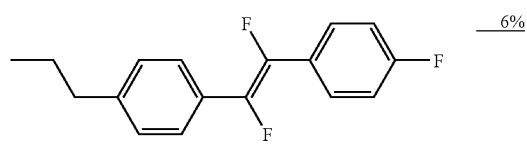

MIXTURE EXAMPLE 22

| | | | |
|---|---|---|---|
| APUQU-2-F | 8% | Clearing point [° C.]: | 73.0 |
| CC-3-V | 25% | Δn [589 nm, 20° C.]: | 0.1005 |
| CC-3-V1 | 13% | Δε [1 kHz, 20° C.]: | +8.6 |
| CCP-V-1 | 10.5% | $\gamma_1$ [mPa · s, 20° C.]: | 59 |
| CCP-V2-1 | 10% | $k_1$ [pN, 20° C.] | 12.8 |
| CDU-2-F | 10% | $k_3/k_1$ [pN, 20° C.] | 1.01 |
| PUQU-2-F | 8.5% | $V_0$ [V, 20° C.] | 1.28 |
| PUQU-3-F | 9% | | |

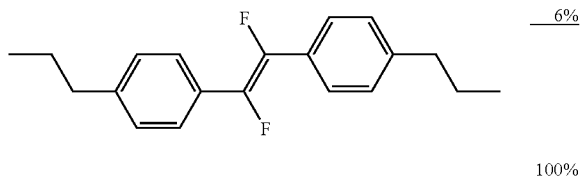

6%

100%

MIXTURE EXAMPLE 23

| | | | |
|---|---|---|---|
| APUQU-2-F | 8% | Clearing point [° C.]: | 74.5 |
| CC-3-V | 26% | Δn [589 nm, 20° C.]: | 0.0996 |
| CC-3-V1 | 12% | Δε [1 kHz, 20° C.]: | +8.5 |
| CCP-V-1 | 10.5% | $\gamma_1$ [mPa · s, 20° C.]: | 59 |
| CCP-V2-1 | 12% | $k_1$ [pN, 20° C.] | 12.7 |
| CDU-2-F | 8% | $k_3/k_1$ [pN, 20° C.] | 1.05 |
| PGU-2-F | 2% | $V_0$ [V, 20° C.] | 1.28 |
| PUQU-2-F | 7.5% | | |
| PUQU-3-F | 8% | | |

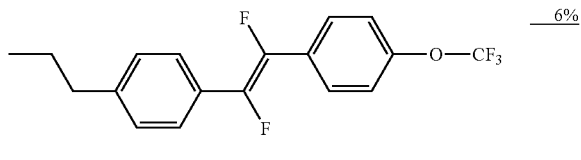

6%

100%

MIXTURE EXAMPLE 24

| | | | |
|---|---|---|---|
| APUQU-2-F | 8% | Clearing point [° C.]: | 73 |
| CC-3-V | 25% | Δn [589 nm, 20° C.]: | 0.1000 |
| CC-3-V1 | 12% | Δε [1 kHz, 20° C.]: | +8.5 |
| CCP-V-1 | 10.5% | $\gamma_1$ [mPa · s, 20° C.]: | 60 |
| CCP-V2-1 | 12% | $k_1$ [pN, 20° C.] | 12.2 |
| CDU-2-F | 9.5% | $k_3/k_1$ [pN, 20° C.] | 1.07 |
| PGU-2-F | 1.5% | $V_0$ [V, 20° C.] | 1.25 |
| PUQU-2-F | 7.5% | | |
| PUQU-3-F | 8% | | |

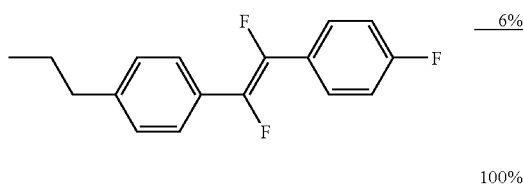

6%

100%

MIXTURE EXAMPLE 25

| | | | |
|---|---|---|---|
| APUQU-2-F | 9% | Clearing point [° C.]: | 78 |
| CC-3-V | 16% | Δn [589 nm, 20° C.]: | 0.1118 |
| CC-3-V1 | 12% | Δε [1 kHz, 20° C.]: | +11.1 |
| CCP-30CF3 | 7% | $\gamma_1$ [mPa · s, 20° C.]: | 74 |
| CCP-V-1 | 11% | | |
| CCP-V2-1 | 10% | | |
| CDU-2-F | 5.5% | | |
| PGU-2-F | 5% | | |
| PUQU-2-F | 10% | | |
| PUQU-3-F | 10% | | |
| 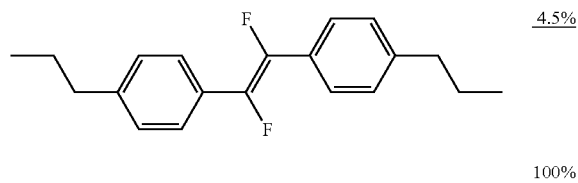 | 4.5% | | |
| | 100% | | |

MIXTURE EXAMPLE 26

| | | | |
|---|---|---|---|
| APUQU-2-F | 9% | Clearing point [° C.]: | 79.5 |
| CC-3-V | 15.5% | Δn [589 nm, 20° C.]: | 0.1112 |
| CC-3-V1 | 12% | Δε [1 kHz, 20° C.]: | +11.1 |
| CCP-30CF3 | 7.5% | $\gamma_1$ [mPa · s, 20° C.]: | 72 |
| CCP-V-1 | 11.5% | | |
| CCP-V2-1 | 11% | | |
| CDU-2-F | 3.5% | | |
| PGU-2-F | 5% | | |
| PUQU-2-F | 10% | | |
| PUQU-3-F | 10% | | |
| 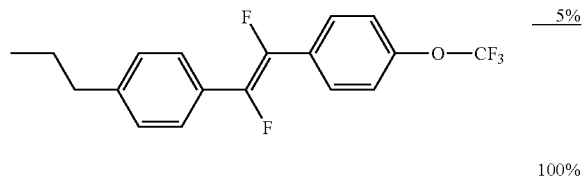 | 5% | | |
| | 100% | | |

MIXTURE EXAMPLE 27

| | | | |
|---|---|---|---|
| APUQU-2-F | 9% | Clearing point [° C.]: | 78.5 |
| CC-3-V | 14.5% | Δn [589 nm, 20° C.]: | 0.1114 |
| CC-3-V1 | 12% | Δε [1 kHz, 20° C.]: | +11.2 |
| CCP-30CF3 | 7.5% | $\gamma_1$ [mPa · s, 20° C.]: | 76 |
| CCP-V-1 | 11.5% | $k_1$ [pN, 20° C.] | 12.7 |
| CCP-V2-1 | 11% | $k_3/k_1$ [pN, 20° C.] | 1.08 |
| CDU-2-F | 5% | $V_0$ [V, 20° C.] | 1.12 |
| PGU-2-F | 4.5% | | |
| PUQU-2-F | 10% | | |
| PUQU-3-F | 10% | | |
| 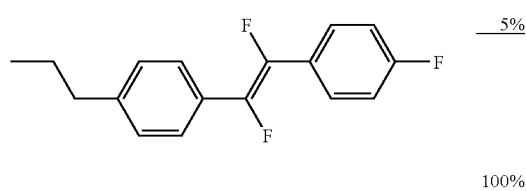 | 5% | | |
| | 100% | | |

MIXTURE EXAMPLE 28

| | | | |
|---|---|---|---|
| CC-3-V | 21% | Clearing point [° C.]: | 74 |
| CC-3-V1 | 6% | Δn [589 nm, 20° C.]: | 0.1192 |
| CCQU-2-F | 11% | Δε [1 kHz, 20° C.]: | +11.2 |
| PUQU-3-F | 17% | $\varepsilon_{\parallel}$ [1 kHz, 20° C.]: | +15.0 |
| PGU-2-F | 7% | $\gamma_1$ [mPa·s, 20° C.]: | 77 |
| PGU-3-F | 12% | $V_{10}$ [V]: | 1.23 |
| CCP-V-1 | 17% | $V_{90}$ [V]: | 1.88 |
| CCGU-3-F | 3% | | |
| 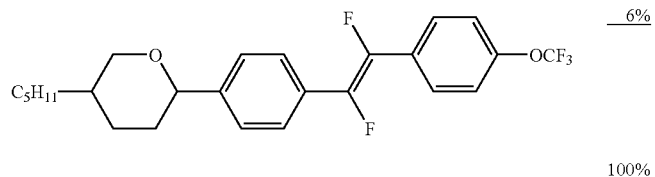 | 6% | | |
| | 100% | | |

MIXTURE EXAMPLE 29

| | | | |
|---|---|---|---|
| CC-3-V | 42% | Clearing point [° C.]: | 75 |
| CC-3-V1 | 12% | Δn [589 nm, 20° C.]: | 0.1210 |
| PP-1-2V1 | 1% | Δε [1 kHz, 20° C.]: | +4.3 |
| PGU-2-F | 8% | $\varepsilon_{\parallel}$ [1 kHz, 20° C.]: | +7.2 |
| PGU-3-F | 12% | $\gamma_1$ [mPa·s, 20° C.]: | 49 |
| PGP-2-3 | 6% | $V_{10}$ [V]: | 2.10 |
| PGP-2-4 | 5% | $V_{90}$ [V]: | 3.08 |
| CCP-V-1 | 6% | | |
| 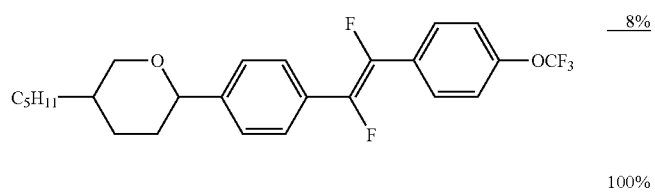 | 8% | | |
| | 100% | | |

MIXTURE EXAMPLE 30

| | | | |
|---|---|---|---|
| CC-3-V | 41% | Clearing point [° C.]: | 74.5 |
| CC-3-V1 | 6% | Δn [589 nm, 20° C.]: | 0.1204 |
| PP-1-2V1 | 3% | Δε [1 kHz, 20° C.]: | +4.0 |
| PGU-2-F | 6% | $\varepsilon_{\parallel}$ [1 kHz, 20° C.]: | +7.1 |
| PGU-3-F | 8% | $\gamma_1$ [mPa·s, 20° C.]: | — |
| PGP-2-3 | 6% | $V_{10}$ [V]: | — |
| PGP-2-4 | 6% | $V_{90}$ [V]: | — |
| CCP-V-1 | 17% | | |
| 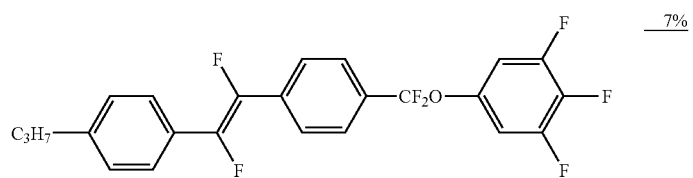 | 7% | | |
| | 100% | | |

MIXTURE EXAMPLE 31

| | | | |
|---|---|---|---|
| CC-3-V | 24% | Clearing point [° C.]: | 75.5 |
| CCQU-2-F | 6% | Δn [589 nm, 20° C.]: | 0.1210 |
| PUQU-3-F | 17% | Δε [1 kHz, 20° C.]: | +12.7 |
| PGU-2-F | 5% | ε∥ [1 kHz, 20° C.]: | +16.4 |
| PGU-3-F | 6% | γ₁ [mPa · s, 20° C.]: | 82 |
| CCP-30CF3 | 8% | $V_{10}$ [V]: | 1.21 |
| PGP-2-3 | 1% | $V_{90}$ [V]: | 1.88 |
| CCP-V-1 | 18% | | |
| CCGU-3-F | 3% | | |

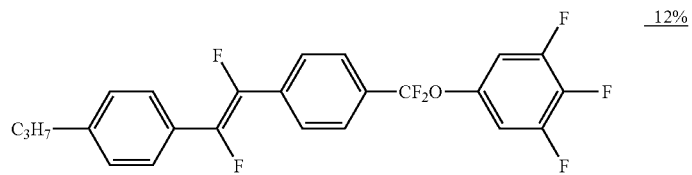

12%

100%

MIXTURE EXAMPLE 32

| | | | |
|---|---|---|---|
| CC-3-V | 24% | Clearing point [° C.]: | 77.5 |
| CCQU-2-F | 6% | Δn [589 nm, 20° C.]: | 0.1209 |
| PUQU-3-F | 17% | Δε [1 kHz, 20° C.]: | +12.2 |
| PGU-2-F | 5% | ε∥ [1 kHz, 20° C.]: | +15.9 |
| PGU-3-F | 6% | γ₁ [mPa · s, 20° C.]: | 78 |
| CCP-30CF3 | 8% | $V_{10}$ [V]: | 1.25 |
| PGP-2-3 | 2% | $V_{90}$ [V]: | 1.90 |
| CCP-V-1 | 18% | | |
| CCGU-3-F | 4% | | |

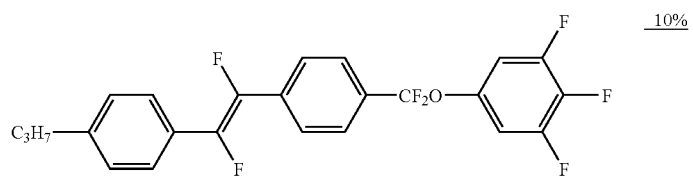

10%

100%

MIXTURE EXAMPLE 33

| | | | |
|---|---|---|---|
| PGU-2-F | 4% | Clearing point [° C.]: | 69 |
| PUQU-2-F | 8% | Δn [589 nm, 20° C.]: | 0.1091 |
| GGP-3-CL | 4% | Δε [1 kHz, 20° C.]: | +4.1 |
| CC-3-V | 35.5% | ε∥ [1 kHz, 20° C.]: | +6.9 |
| CC-3-V1 | 13% | γ₁ [mPa · s, 20° C.]: | 47 |
| PP-1-2V1 | 9% | $k_1$ [pN, 20° C.] | 13.0 |
| CCP-V-1 | 11% | $k_3/k_1$ [pN, 20° C.] | 1.06 |
| CCP-V2-1 | 2.5% | $V_0$ [V, 20° C.] | 1.88 |

| | -continued | |
|---|---|---|
| BCH-32 | | 8% |
| | | 5% |

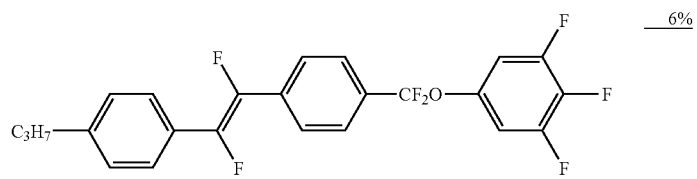

| | | 100% |

MIXTURE EXAMPLE 34

| | | | | |
|---|---|---|---|---|
| CDU-2-F | 2% | Clearing point [° C.]: | 75.5 |
| PGU-2-F | 3% | Δn [589 nm, 20° C.]: | 0.0996 |
| PUQU-2-F | 7.5% | Δε [1 kHz, 20° C.]: | +8.7 |
| PUQU-3-F | 8% | $\epsilon_{\parallel}$ [1 kHz, 20° C.]: | +12.1 |
| CCP-V-1 | 11% | $\gamma_1$ [mPa·s, 20° C.]: | 59 |
| CCP-V2-1 | 11.5% | $k_1$ [pN, 20° C.] | 12.4 |
| CC-3-V1 | 12.5% | $k_3/k_1$ [pN, 20° C.] | 1.12 |
| CC-3-V | 30.5% | $V_0$ [V, 20° C.] | 1.25 |
| APUQU-2-F | 8% | | |

| | | 6% |

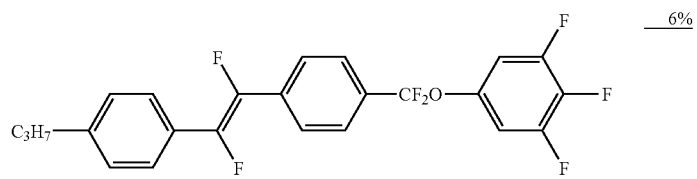

| | | 100% |

MIXTURE EXAMPLE 35

| | | | | |
|---|---|---|---|---|
| CDU-2-F | 4.5% | Clearing point [° C.]: | 74 |
| PGU-2-F | 5% | Δn [589 nm, 20° C.]: | 0.1000 |
| PUQU-2-F | 8% | Δε [1 kHz, 20° C.]: | +8.6 |
| PUQU-3-F | 8% | $\epsilon_{\parallel}$ [1 kHz, 20° C.]: | +12.1 |
| CCP-V-1 | 11% | $\gamma_1$ [mPa·s, 20° C.]: | 60 |
| CCP-V2-1 | 6% | $k_1$ [pN, 20° C.] | 12.1 |
| CC-3-V1 | 12% | $k_3/k_1$ [pN, 20° C.] | 1.10 |
| CC-3-V | 31.5% | $V_0$ [V, 20° C.] | 1.25 |
| APUQU-2-F | 8% | | |

| | | 6% |

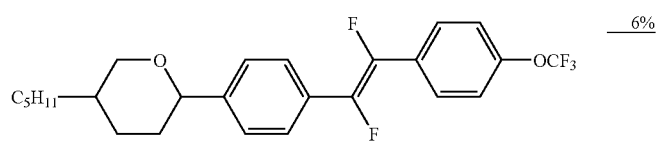

| | | 100% |

MIXTURE EXAMPLE 36

| | | | |
|---|---|---|---|
| CCP-30CF3 | 7% | Clearing point [° C.]: | 80 |
| PGU-2-F | 5.5% | $\Delta n$ [589 nm, 20° C.]: | 0.1096 |
| PUQU-2-F | 8.5% | $\Delta \epsilon$ [1 kHz, 20° C.]: | +10.9 |
| PUQU-3-F | 9% | $\epsilon_{\parallel}$ [1 kHz, 20° C.]: | +14.4 |
| CC-3-V1 | 12% | $\gamma_1$ [mPa · s, 20° C.]: | 71 |
| CC-3-V | 21.5% | $k_1$ [pN, 20° C.] | 13.0 |
| CCP-V-1 | 11.5% | $k_3/k_1$ [pN, 20° C.] | 1.08 |
| CCP-V2-1 | 10% | $V_0$ [V, 20° C.] | 1.15 |
| APUQU-2-F | 8.5% | | |

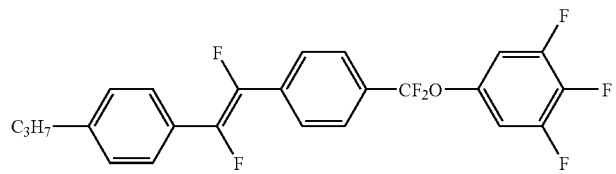

6.5%

100%

MIXTURE EXAMPLE 37

| | | | |
|---|---|---|---|
| PUQU-2-F | 11% | Clearing point [° C.]: | 75 |
| PUQU-3-F | 9.5% | $\Delta n$ [589 nm, 20° C.]: | 0.1001 |
| CCP-30CF3 | 8% | $\Delta \epsilon$ [1 kHz, 20° C.]: | +13.9 |
| CC-3-V | 25% | $\epsilon_{\parallel}$ [1 kHz, 20° C.]: | +17.9 |
| CC-3-V1 | 11% | $\gamma_1$ [mPa · s, 20° C.]: | 79 |
| CCZU-3-F | 1.5% | $k_1$ [pN, 20° C.] | 11.4 |
| CCQU-3-F | 10% | $k_3/k_1$ [pN, 20° C.] | 1.11 |
| CCGU-3-F | 10% | $V_0$ [V, 20° C.] | 0.96 |
| APUQU-2-F | 9% | | |

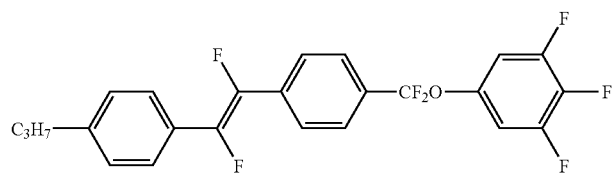

5%

100%

MIXTURE EXAMPLE 38

| | | | |
|---|---|---|---|
| PUQU-2-F | 11% | Clearing point [° C.]: | 75.5 |
| PUQU-3-F | 9.5% | $\Delta n$ [589 nm, 20° C.]: | 0.0996 |
| CCZU-3-F | 9.5% | $\Delta \epsilon$ [1 kHz, 20° C.]: | +13.4 |
| CC-3-V | 35% | $\epsilon_{\parallel}$ [1 kHz, 20° C.]: | +17.5 |
| CCQU-3-F | 10% | $\gamma_1$ [mPa · s, 20° C.]: | 80 |
| CCGU-3-F | 9% | $k_1$ [pN, 20° C.] | 11.0 |
| APUQU-2-F | 9% | $k_3/k_1$ [pN, 20° C.] | 1.07 |
| | | $V_0$ [V, 20° C.] | 0.95 |

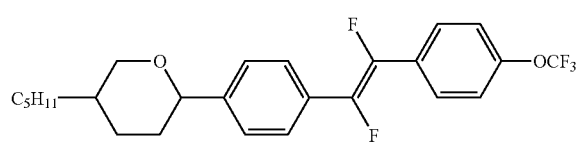

7%

100%

What is claimed is:

1. A liquid-crystalline medium of positive dielectric anisotropy based on a mixture of compounds, said medium comprising one or more compounds of the formula I

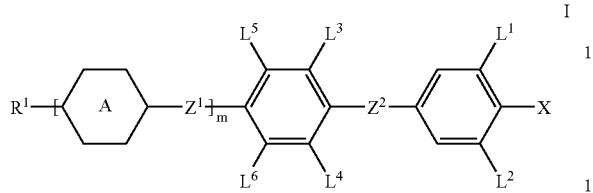

in which

R$^1$ is a halogenated or unsubstituted alkyl or alkoxy radical having 1 to 15 C atoms, where, in addition, one or more CH$_2$ groups in these radicals are each, independently of one another, optionally replaced by —C≡C—, —CH=CH—, —O—, —CO—O— or —O—CO— in such a way that O atoms are not linked directly to one another, ring A is a ring system of the formulae

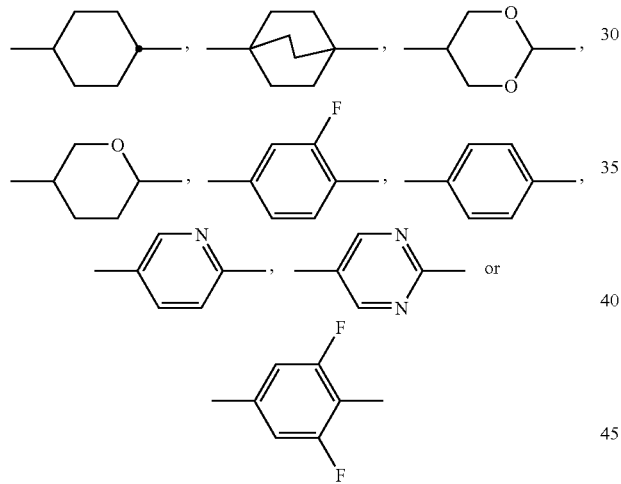

pointing to the left or right,

Z$^1$, Z$^2$ are each, independently, a single bond, —C≡C—, —CF=CF—, —CH=CH—, —CF$_2$O— or —CH$_2$CH$_2$—, where at least one of Z$^1$ and Z$^2$ is —CF=CF—, X is F, Cl, CN, SF$_5$ or a halogenated or unsubstituted alkyl or alkoxy radical having 1 to 15 C atoms, where, in addition, one or more CH$_2$ groups in these radicals are each, independently of one another, optionally replaced by —C≡C—, —CH=CH—, —O—, —CO—O— or —O—CO— in such a way that O atoms are not linked directly to one another, L$^1$, L$^2$, L$^3$, L$^4$, L$^5$ and L$^6$ are each, independently of one another, H or F, and m is 0 or 1; and said medium further comprises one or more compounds of formulae K-1 to K-12:

K-1
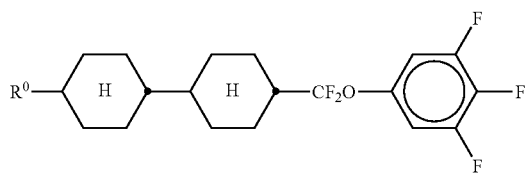

K-2
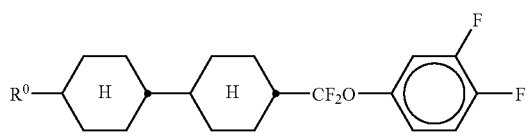

K-3
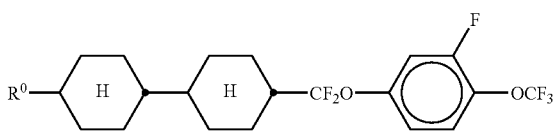

K-4
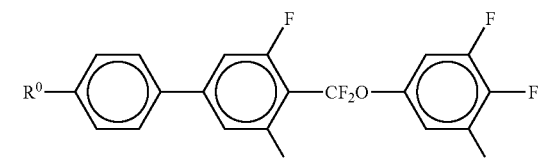

K-5
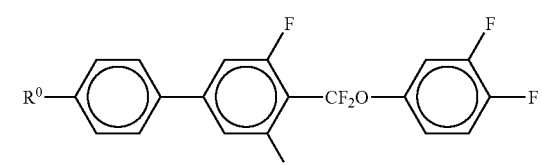

K-6
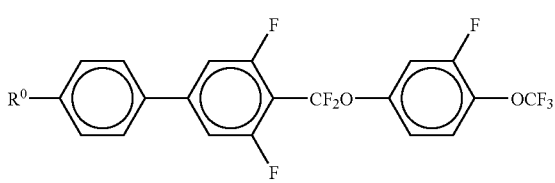

K-7
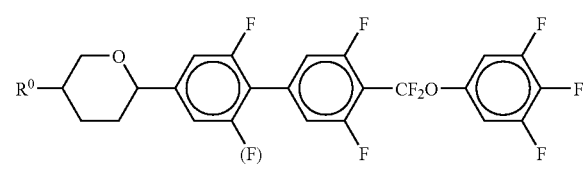

K-8
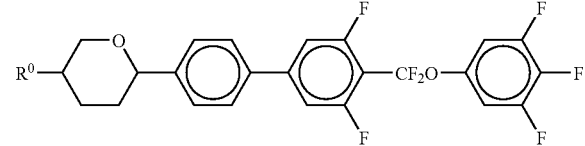

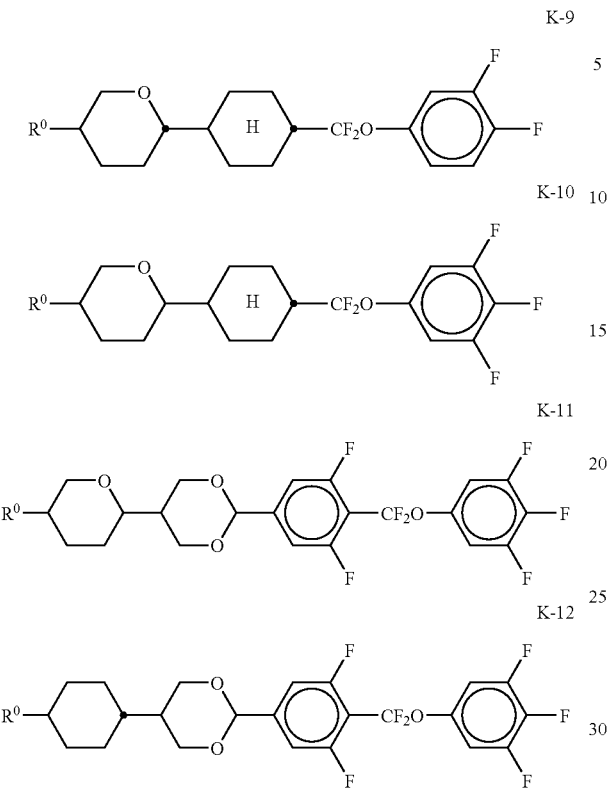
in which
R⁰ is n-alkyl, oxaalkyl, fluoroalkyl or alkenyl, each having up to 9 C atoms.
2. A liquid-crystalline medium according to claim 1, wherein said medium comprises one, two or more compounds of the formulae I-1 to I-30:
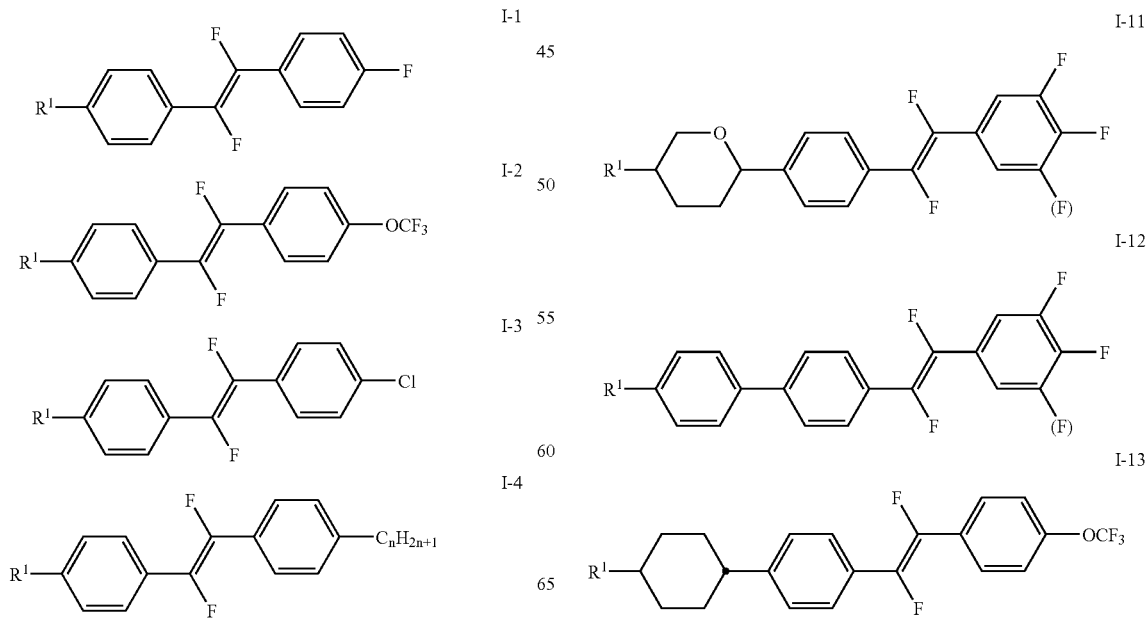

-continued in which
R¹ is a halogenated or unsubstituted alkyl or alkoxy radical having 1 to 15 C atoms, where, in addition, one or more CH₂ groups in these radicals are each, independently of one another, optionally replaced by —C≡C—, —CH=CH—, —O—, —CO—O— or —O—CO— in such a way that O atoms are not linked directly to one another, and n stands for 1, 2, 3, 4, 5, 6, 7 or 8.

3. A liquid-crystalline medium according to claim 1, wherein said medium further comprises one or more compounds of formulae Z-1 to Z-9:

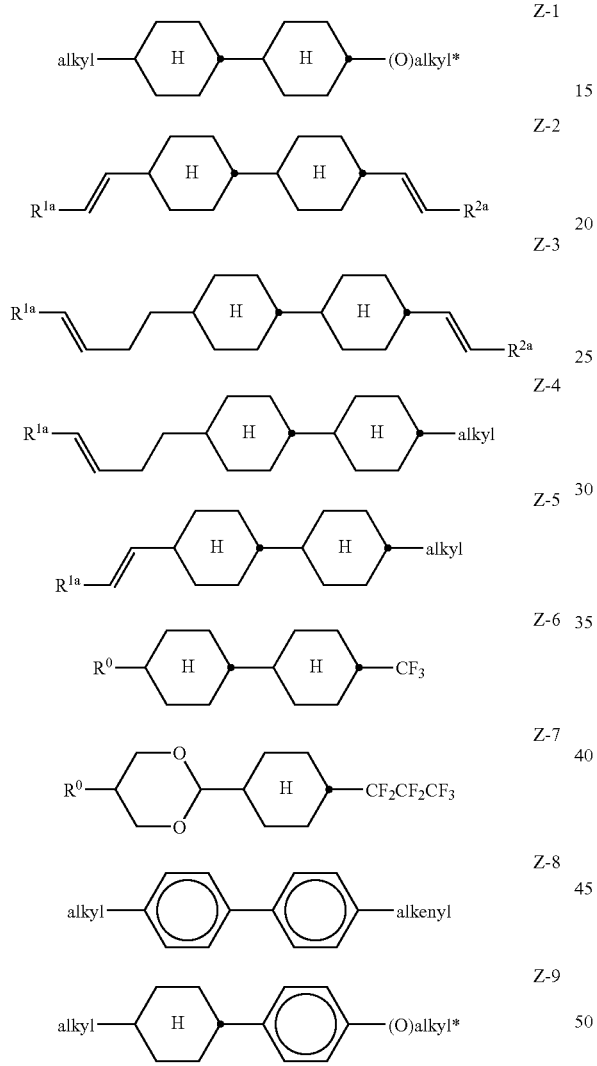

in which
- $R^{1a}$ and $R^{2a}$ are each, independently of one another, H, $CH_3$, $C_2H_5$ or $n\text{-}C_3H_7$,
- alkyl, alkyl* are each, independently, an unsubstituted n-alkyl radical having 1 to 7 C atoms, and
- alkenyl is an unsubstituted alkenyl radical having 2-7 C atoms.

4. A liquid-crystalline medium according to claim 1, wherein said medium further comprises one or more compounds selected from formulae II, III, IV, V and VI

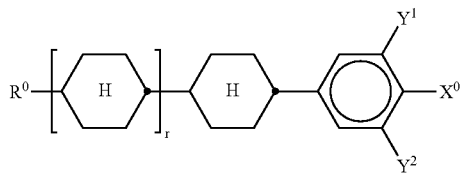

in which
- $R^0$ is n-alkyl, oxaalkyl, fluoroalkyl or alkenyl, each having up to 9 C atoms,
- $X^0$ is F, Cl, halogenated alkyl having up to 6 C atoms, halogenated alkenyl having up to 6 C atoms, halogenated alkenyloxy having up to 6 C atoms, or halogenated alkoxy having up to 6 C atoms,
- $Z^0$ is —$C_2F_4$—, —CF=CF—, —$C_2H_4$—, —$(CH_2)_4$—, —$OCH_2$—, —$CH_2O$—, —$CF_2O$— or —$OCF_2$—,
- $Y^1$ to $Y^4$ are each, independently of one another, H or F,
- r is 0 or 1, and
- t is 0, 1 or 2.

5. A liquid-crystalline medium according claim 1, wherein said medium further comprises one or more compounds selected from formulae XIV and XV:

in which
- $R^0$ is n-alkyl, oxaalkyl, fluoroalkyl or alkenyl, each having up to 9 C atoms,
- $X^0$ is F, Cl, halogenated alkyl having up to 6 C atoms, halogenated alkenyl having up to 6 C atoms, halogenated alkenyloxy having up to 6 C atoms, or halogenated alkoxy having up to 6 C atoms,
- rings A and B, independently of one another, are each 1,4-phenylene which is substituted by 0, 1 or 2 fluorine, and
- where in each case at least one of the 1,4-phenylene rings is mono- or polysubstituted by fluorine atoms.

6. A liquid-crystalline medium according to claim 1, wherein said medium further comprises one or more compounds of formulae E-a to E-d

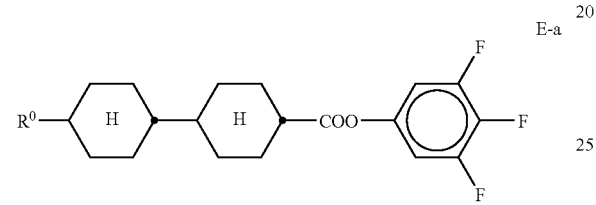
E-a

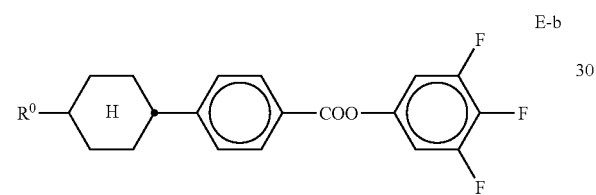
E-b

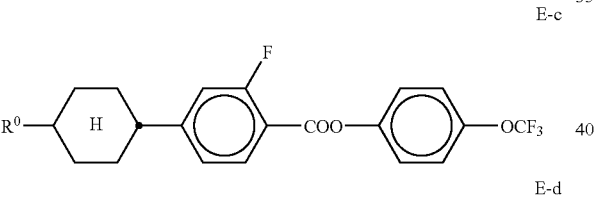
E-c

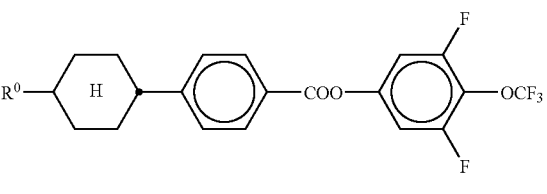
E-d in which
- $R^0$ is n-alkyl, oxaalkyl, fluoroalkyl or alkenyl, each having up to 9 C atoms.

7. A liquid-crystalline medium according to claim 1, wherein said medium further comprises one or more compounds of formulae IIa to IIg

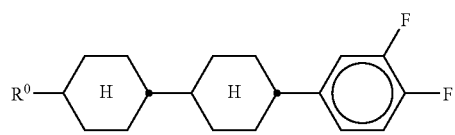
IIa

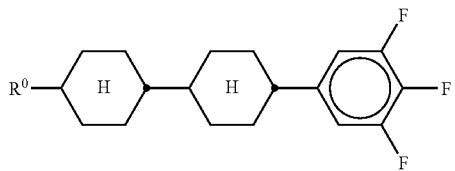
IIb

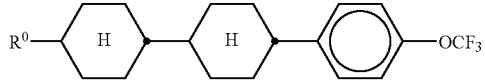
IIc

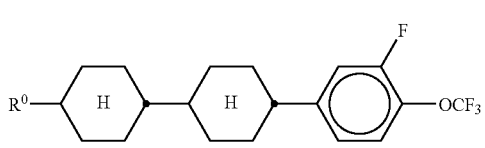
IId

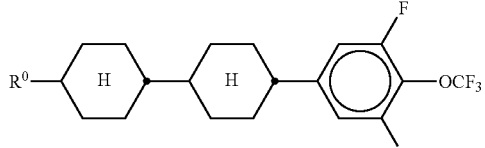
IIe

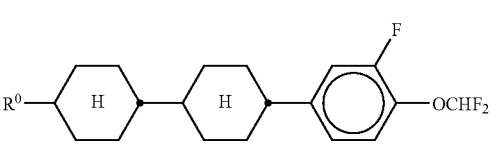
IIf

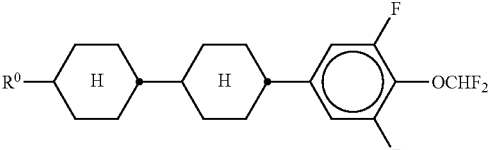
IIg in which
- $R^0$ is n-alkyl, oxaalkyl, fluoroalkyl or alkenyl, each having up to 9 C atoms.

8. A liquid-crystalline medium according to claim 1, wherein said medium further comprises one or more compounds of formulae O1 and O2

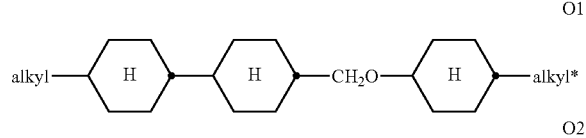
O1

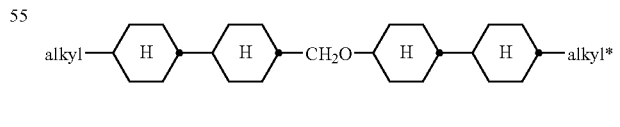
O2 in which
- alkyl and alkyl* are each, independently of one another, a straight-chain or branched alkyl group having 1-7 carbon atoms.

9. A liquid-crystalline medium according to claim 1, wherein said medium further comprises one or more dioxane compounds of formulae D1 and/or D2

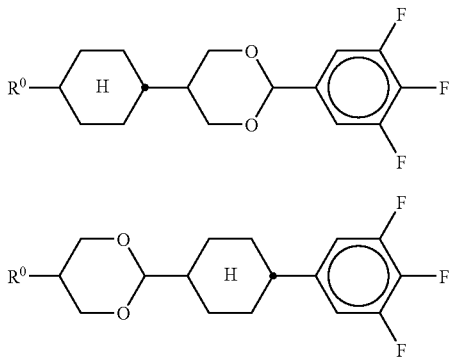

in which
R⁰ is n-alkyl, oxaalkyl, fluoroalkyl or alkenyl, each having up to 9 C atoms.

10. In a method of generating an electro-optical effect using a liquid-crystalline medium, the improvement wherein said medium is a liquid-crystalline medium according to claim 1.

11. An electro-optical liquid-crystal display containing a liquid-crystalline medium according to claim 1.

12. A compound according to formula Ic

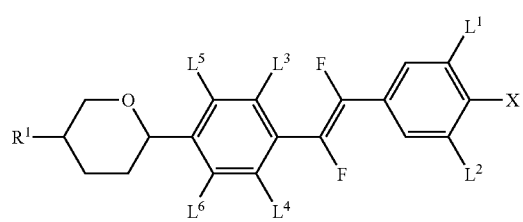

in which
R¹ is a halogenated or unsubstituted alkyl or alkoxy radical having 1 to 15 C atoms, where, in addition, one or more CH₂ groups in these radicals are each, independently of one another, optionally replaced by —C≡C—, —CH=CH—, —O—, —CO—O— or —O—CO— in such a way that O atoms are not linked directly to one another, X is F, Cl, CN, SF₅ or a halogenated or unsubstituted alkyl or alkoxy radical having 1 to 15 C atoms, where, in addition, one or more CH₂ groups in these radicals are each, independently of one another, optionally replaced by —C≡C—, —CH=CH—, —O—, —CO—O— or —O—CO— in such a way that O atoms are not linked directly to one another, and L¹, L², L³, L⁴, L⁵ and L⁶ are each, independently of one another, H or F.

13. A liquid-crystalline medium according to claim 1, wherein 2, 3 or 4 of the substituents L¹, L², L³ and L⁴ in the formula I are each hydrogen and the others are each F.

14. A liquid-crystalline medium according to claim 1, wherein L⁵ and L⁶ are each H.

15. A liquid-crystalline medium according to claim 1, wherein m is 0, and L¹ or L² are each F; or m is 1 or 2, and L¹ and L² are each H.

16. A liquid-crystalline medium according to claim 1, wherein X is F, Cl, OCF₃, CF₃, SF₅, OCHF₂, OC₂F₅, OC₃F₇, OCHFCF₃, OCF₂CHFCF₃ or alkyl having 1 to 8 C atoms.

17. A liquid-crystalline medium according to claim 1, wherein R¹ is an unsubstituted, straight-chain alkyl having 1 to 6 C atoms, straight-chain alkoxy having 1 to 6 C atoms, or straight-chain 2-6 C alkenyl.

18. A liquid-crystalline medium according to claim 1, wherein Z¹ is a single bond or —CF=CF—, Z² is —CF=CF— or —CF₂O—, and m is 0 or 1.

19. A liquid-crystalline medium according to claim 1, wherein m is 1 or 2, Z¹ is —CF=CF—, and ring A is a ring system selected from the formulae

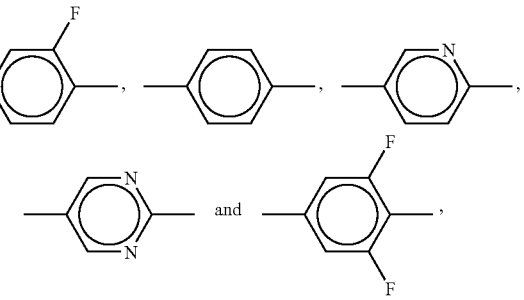

where the rings may point to both sides.

20. A liquid-crystalline medium according to claim 1, wherein m is 1 or 2, Z is —CF=CF—, and ring A is a ring system selected from the formulae

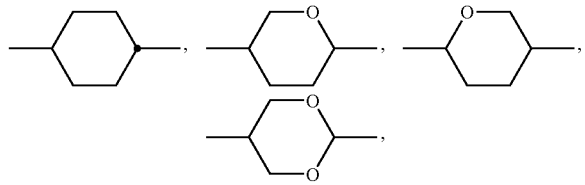

and

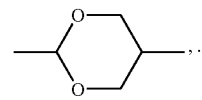

21. A liquid-crystalline medium according to claim 1, wherein
m is 1,
Z² is —CF=CF— and Z¹ is a single bond,
X is F, —OCF₃, —CF₃, CN, 1-6 C n-alkyl or 1-6 C n-alkoxy,
L⁵, L⁶ are each H, or
R¹ is 1-7 C alkyl or 2-7 C alkylene.

22. A liquid-crystalline medium according to claim 1, wherein Z² is —CF=CF—, and L³ and L⁴ are each H.

23. A liquid-crystalline medium according to claim 1, wherein said medium has a rotational viscosity γ₁ at 20° C. of <80 mPa·s.

24. A liquid-crystalline medium according to claim 1, wherein said medium has a flow viscosity $v_{20}$ at 20° C. of <50 mm$^2 \cdot$s$^{-1}$.

25. A liquid-crystalline medium according to claim 1, wherein the proportion of compounds of the formula I in the mixture as a whole is from 0.5 to 40% by weight, and the proportion of compounds of formulae K-1 to K-12 from 5 to 50% by weight.

26. A liquid-crystalline medium according to claim 4, wherein the proportion of compounds of formulae II to VI in the mixture as a whole is from 30 to 80% by weight.

27. A liquid-crystalline medium according to claim 26, wherein the proportion of compounds of the formula I in the mixture as a whole is from 0.5 to 40% by weight, and the proportion of compounds of formulae K-1 to K-12 from 5 to 50% by weight.

28. A liquid-crystalline medium according to claim 6, wherein the proportion of the compounds of formulae E-a to E-d in the mixture as a whole is 5-30% by weight.

* * * * *

UNITED STATES PATENT AND TRADEMARK OFFICE
CERTIFICATE OF CORRECTION

PATENT NO. : 7,651,742 B2  Page 1 of 1
APPLICATION NO. : 11/917284
DATED : January 26, 2010
INVENTOR(S) : Wittek et al.

It is certified that error appears in the above-identified patent and that said Letters Patent is hereby corrected as shown below:

Column 90, line 32 reads "wherein m is 1 or 2, Z is -CF=CF-, and ring A is a ring" should read -- wherein m is 1 or 2, $Z^2$ is -CF=CF-, and ring A is a ring --

Signed and Sealed this

Ninth Day of November, 2010

David J. Kappos
*Director of the United States Patent and Trademark Office*